(12) United States Patent
Williams et al.

(10) Patent No.: US 11,850,093 B2
(45) Date of Patent: *Dec. 26, 2023

(54) SURGICAL SYSTEM WITH COMBINED LASER ABLATION/ IMAGING TOOL

(71) Applicant: Intuitive Surgical Operations, Inc., Sunnyvale, CA (US)

(72) Inventors: Matthew R. Williams, Walnut Creek, CA (US); Gregory W. Dachs, II, Sunnyvale, CA (US); David Shafer, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 17/305,334

(22) Filed: Jul. 6, 2021

(65) Prior Publication Data

US 2022/0000452 A1    Jan. 6, 2022

Related U.S. Application Data

(63) Continuation of application No. 16/531,814, filed on Aug. 5, 2019, now Pat. No. 11,051,788, which is a
(Continued)

(51) Int. Cl.
*A61B 18/20* (2006.01)
*A61B 8/00* (2006.01)
(Continued)

(52) U.S. Cl.
CPC .............. *A61B 8/4488* (2013.01); *A61B 8/12* (2013.01); *A61B 8/445* (2013.01); *A61B 18/22* (2013.01); *A61B 34/30* (2016.02); *A61B 34/37* (2016.02); *A61B 34/71* (2016.02); *A61B 90/30* (2016.02); *A61B 90/361* (2016.02);
(Continued)

(58) Field of Classification Search
CPC .......... A61B 18/20; A61B 34/30; A61B 34/70
See application file for complete search history.

(56) References Cited

U.S. PATENT DOCUMENTS

| 636,488 A | 11/1899 | Catanzano |
|---|---|---|
| 3,858,577 A | 1/1975 | Bass et al. |

(Continued)

OTHER PUBLICATIONS

GE PLASTICS, "Ultem PEI Resin Product Guide," 52 pages, 2003.
(Continued)

*Primary Examiner* — Lynsey C Eiseman
(74) *Attorney, Agent, or Firm* — Alford law Group, Inc.; Vy H. Vu; William E. Alford

(57) ABSTRACT

In one embodiment of the invention, a robotic surgical system includes a combined laser imaging robotic surgical tool, a control console, and a laser generator/controller. The tool is mounted to a first robotic arm of a patient side cart. The tool has a wristed joint and an end effector coupled together. The end effector has a laser-emitting device to direct a laser beam onto tissue in a surgical site and an image-capturing device to capture images of the tissue in the surgical site. The control console, in communication with the tool, receives the captured images of tissue in the surgical site and displays the captured images on a display device to a user. The laser generator/controller is coupled to the tool and the control console to control the emission of the laser beam onto tissue of the surgical site.

17 Claims, 18 Drawing Sheets

Related U.S. Application Data continuation of application No. 12/060,112, filed on Mar. 31, 2008, now Pat. No. 10,368,838.

(51) Int. Cl.

| | |
|---|---|
| *A61B 18/22* | (2006.01) |
| *A61B 8/12* | (2006.01) |
| *A61B 34/00* | (2016.01) |
| *A61B 90/30* | (2016.01) |
| *A61B 34/30* | (2016.01) |
| *A61B 34/37* | (2016.01) |
| *A61B 90/00* | (2016.01) |
| *A61B 17/00* | (2006.01) |

(52) U.S. Cl.
CPC ............ *A61B 2017/00477* (2013.01); *A61B 2018/2025* (2013.01); *A61B 2034/305* (2016.02); *A61B 2090/3614* (2016.02); *A61B 2090/371* (2016.02); *A61B 2090/378* (2016.02)

(56) References Cited

U.S. PATENT DOCUMENTS

| | | |
|---|---|---|
| 4,266,549 A | 5/1981 | Kimura |
| 4,408,602 A | 10/1983 | Nakajima |
| 4,419,987 A | 12/1983 | Ogiu |
| 4,458,683 A | 7/1984 | Saito et al. |
| 4,503,854 A | 3/1985 | Jako |
| 4,635,644 A | 1/1987 | Yagata |
| 4,681,103 A | 7/1987 | Boner et al. |
| 4,742,829 A | 5/1988 | Law et al. |
| 4,838,506 A | 6/1989 | Cooper |
| 4,895,145 A | 1/1990 | Joffe et al. |
| 4,984,563 A | 1/1991 | Renaud |
| 5,049,147 A | 9/1991 | Danon |
| 5,098,426 A | 3/1992 | Sklar et al. |
| 5,121,740 A | 6/1992 | Uram |
| 5,147,354 A | 9/1992 | Boutacoff et al. |
| 5,163,935 A | 11/1992 | Black et al. |
| 5,163,936 A | 11/1992 | Black et al. |
| 5,199,944 A | 4/1993 | Cosmescu |
| 5,269,307 A | 12/1993 | Fife et al. |
| 5,313,962 A | 5/1994 | Obenchain |
| 5,333,603 A | 8/1994 | Schuman |
| 5,337,732 A | 8/1994 | Grundfest et al. |
| 5,368,015 A | 11/1994 | Wilk |
| 5,368,496 A | 11/1994 | Ranalletta et al. |
| 5,368,560 A | 11/1994 | Rambo et al. |
| 5,413,107 A | 5/1995 | Oakley et al. |
| 5,469,853 A | 11/1995 | Law et al. |
| 5,487,740 A | 1/1996 | Sulek et al. |
| 5,503,152 A | 4/1996 | Oakley et al. |
| 5,507,742 A | 4/1996 | Long et al. |
| 5,624,382 A | 4/1997 | Oppelt et al. |
| 5,630,419 A | 5/1997 | Ranalletta |
| 5,709,677 A | 1/1998 | Slatkine |
| 5,807,242 A | 9/1998 | Scheller et al. |
| 5,844,349 A | 12/1998 | Oakley et al. |
| 5,846,182 A | 12/1998 | Wolcott |
| 5,861,002 A | 1/1999 | Desai |
| 5,876,345 A | 3/1999 | Eaton et al. |
| 5,891,039 A | 4/1999 | Bonnefous et al. |
| 5,893,828 A | 4/1999 | Uram |
| 5,931,787 A | 8/1999 | Dietz et al. |
| 5,957,933 A | 9/1999 | Yanof et al. |
| 5,989,182 A | 11/1999 | Hori et al. |
| 6,058,323 A | 5/2000 | Lemelson |
| 6,066,096 A | 5/2000 | Smith et al. |
| 6,088,894 A | 7/2000 | Oakley et al. |
| 6,099,522 A | 8/2000 | Knopp et al. |
| 6,106,517 A | 8/2000 | Zupkas |
| 6,283,920 B1 | 9/2001 | Eberle et al. |
| 6,302,311 B1 | 10/2001 | Adams et al. |
| 6,383,179 B1 | 5/2002 | Neuberger |
| 6,396,198 B1 | 5/2002 | Okimura et al. |
| 6,423,002 B1 | 7/2002 | Hossack |
| 6,673,065 B1 | 1/2004 | Veligdan |
| 6,755,647 B2 | 6/2004 | Melikechi et al. |
| 6,783,524 B2 | 8/2004 | Anderson et al. |
| 6,788,018 B1 | 9/2004 | Blumenkranz |
| 6,817,974 B2 | 11/2004 | Cooper et al. |
| 6,882,117 B1 | 4/2005 | Hughes et al. |
| 6,984,205 B2 | 1/2006 | Gazdzinski |
| 7,090,683 B2 | 8/2006 | Brock et al. |
| 7,094,200 B2 | 8/2006 | Katzman |
| 7,097,640 B2 | 8/2006 | Wang et al. |
| 7,189,226 B2 | 3/2007 | Auld et al. |
| 7,217,266 B2 | 5/2007 | Anderson et al. |
| 7,367,973 B2 | 5/2008 | Manzo et al. |
| 10,368,838 B2 | 8/2019 | Williams et al. |
| 2002/0183809 A1 | 12/2002 | Oron et al. |
| 2004/0082939 A1 | 4/2004 | Berlin |
| 2004/0176753 A1 | 9/2004 | Dick et al. |
| 2004/0261179 A1 | 12/2004 | Blumenkranz |
| 2005/0033270 A1 | 2/2005 | Ramans et al. |
| 2005/0107808 A1 | 5/2005 | Evans et al. |
| 2005/0182298 A1 | 8/2005 | Ikeda et al. |
| 2005/0222554 A1 | 10/2005 | Wallace et al. |
| 2006/0178556 A1 | 8/2006 | Hasser et al. |
| 2006/0199999 A1 | 9/2006 | Ikeda et al. |
| 2006/0271024 A1 | 11/2006 | Gertner et al. |
| 2007/0043338 A1 | 2/2007 | Moll et al. |
| 2008/0027464 A1 | 1/2008 | Moll et al. |
| 2008/0064927 A1 | 3/2008 | Larkin et al. |
| 2008/0065105 A1 | 3/2008 | Larkin et al. |
| 2008/0065107 A1 | 3/2008 | Larkin et al. |
| 2008/0065108 A1 | 3/2008 | Diolaiti |
| 2008/0071291 A1 | 3/2008 | Duval et al. |
| 2008/0081950 A1 | 4/2008 | Koenig et al. |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Wikipedia, "D-Subminiature," 4 pages, downloaded Dec. 1, 2007 at 1:34 a.m., Internet: http://en.wikipedia.org/wiki/D-subminiature.

W.L. Gore & Associates, "Gore Tetrad VersaPlane Laparoscopic Probes," Data Sheet, 2 pages, 2006.

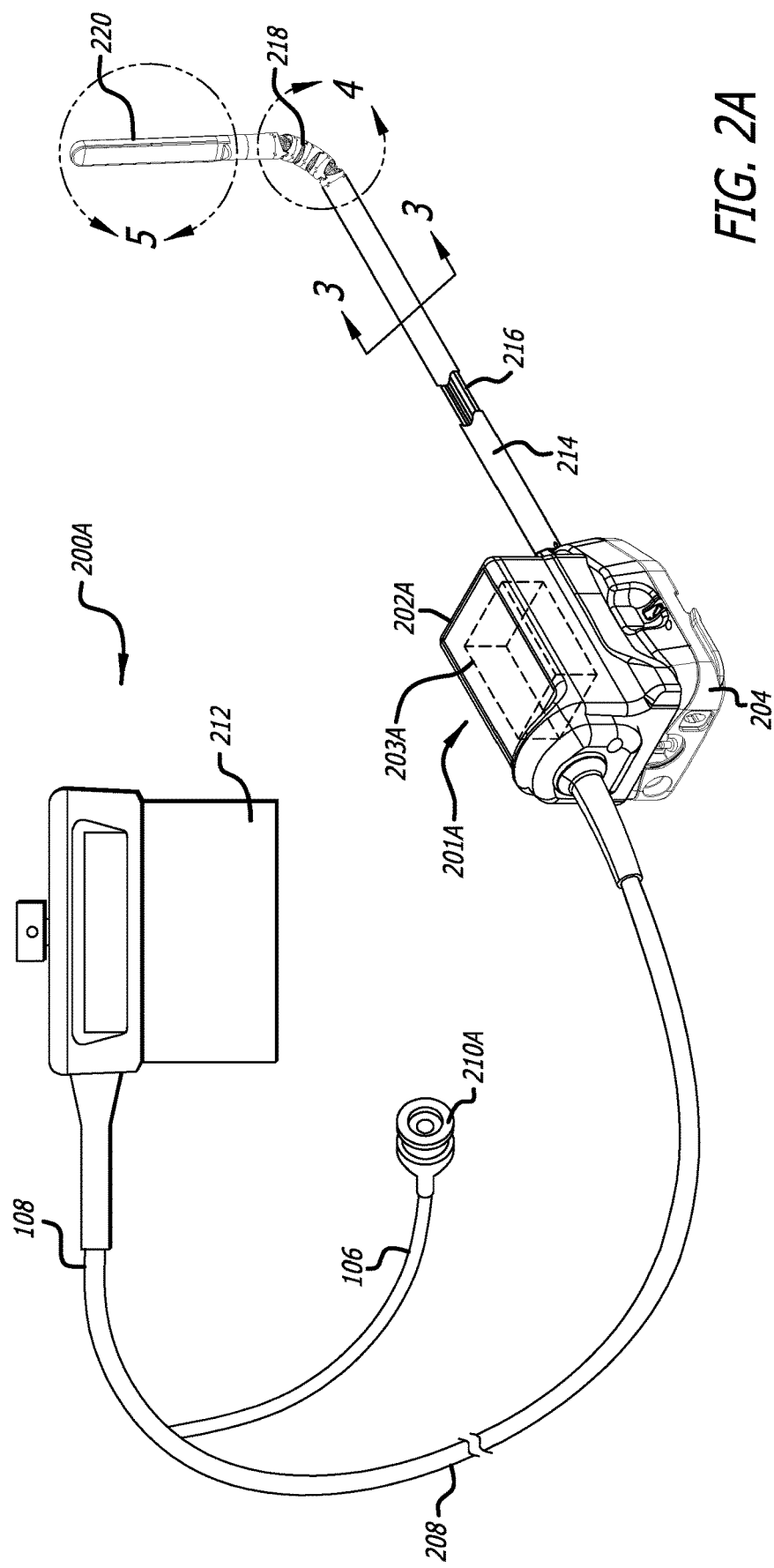

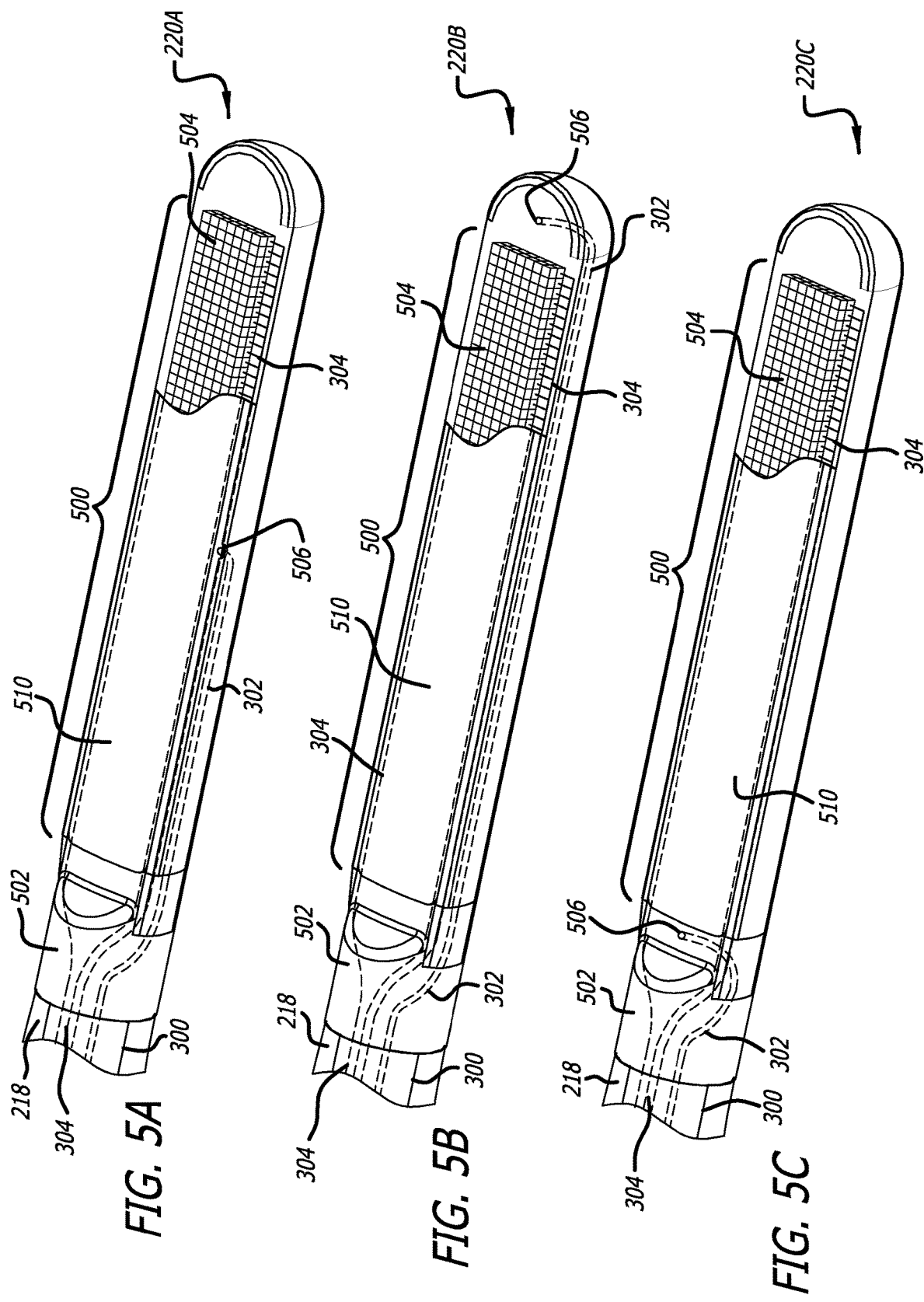

SURGICAL SYSTEM WITH COMBINED LASER ABLATION/ IMAGING TOOL

CROSS REFERENCE TO RELATED APPLICATIONS

This non-provisional patent application claims the benefit of and is a continuation application of U.S. patent application Ser. No. 16/531,814, entitled SURGICAL SYSTEM WITH COMBINED LASER ULTRASOUND IMAGING SURGICAL TOOL FOR LASER MARKING AND ULTRASOUND IMAGING, issued on Jul. 6, 2021 as U.S. Pat. No. 11,051,788. U.S. patent application Ser. No. 16/531,814 is also a non-provisional patent application that claims the benefit of and is a divisional continuation application of U.S. patent application Ser. No. 12/060,112, entitled SURGICAL TOOLS FOR LASER MARKING AND LASER CUTTING filed by Matthew R. Williams et al. on Mar. 31, 2008, now allowed issued on Aug. 6, 2019 as U.S. Pat. No. 10,368,838.

This non-provisional patent application claims the benefit of and is a divisional application of U.S. patent application Ser. No. 12/060,112, entitled SURGICAL TOOLS FOR LASER MARKING AND LASER CUTTING filed by Matthew R. Williams et al. on Mar. 31, 2008, now allowed.

FIELD

The embodiments of the invention generally relate to robotic surgical instruments.

BACKGROUND

Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools.

In endoscopic surgery, the working tools are similar to those used in conventional (open) surgery, except that the working end or end effector of each tool is separated from its handle by an extension tube. As used herein, the term end effector means the actual working part of the surgical instrument and can include clamps, graspers, scissors, staplers, and needle holders, for example.

To perform endoscopic surgical procedures, the surgeon passes these working tools or instruments through the cannula sleeves to an internal surgical site and manipulates them from outside the abdomen. The surgeon may monitor the procedure within the internal surgical site by means of a laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

Minimally invasive surgeries are also being performed on other areas of the body including the neck and throat regions. The neck and throat is a highly visible region and scarring is undesirable for aesthetic and health privacy reasons, thus a minimally invasive procedure is desirable. A readily visible thyroid surgical scar may announce underlying health issues that a patient may not wish disclosed. Due to the lack of skin folds in the throat and neck region, hiding a surgical scar may be problematic. In warmer climes, it is preferable to avoid covering up throat surgery scars with clothing. Operating in a long narrow enclosed space such as the laryngopharynx is challenging due to space restrictions and the accessibility of the surgical site. In these cases, multiple entry ports may not preferred because of visible scarring and limited space.

BRIEF SUMMARY

The embodiments of the invention are summarized by the claims that follow below.

BRIEF DESCRIPTION OF THE DRAWING

FIGS. 2A-2B illustrate perspective views of exemplary embodiments of combined laser ultrasound robotic surgical instruments.

FIGS. 5A-5C are magnified views of exemplary embodiments of the combined laser and ultrasound end effector of the exemplary embodiments of the combined laser ultrasound robotic surgical instruments illustrated in FIGS. 2A-2B.

Similar reference numbers in the different drawings are associated with the same or similar elements but may have a different configuration.

DETAILED DESCRIPTION

Figure 1A:
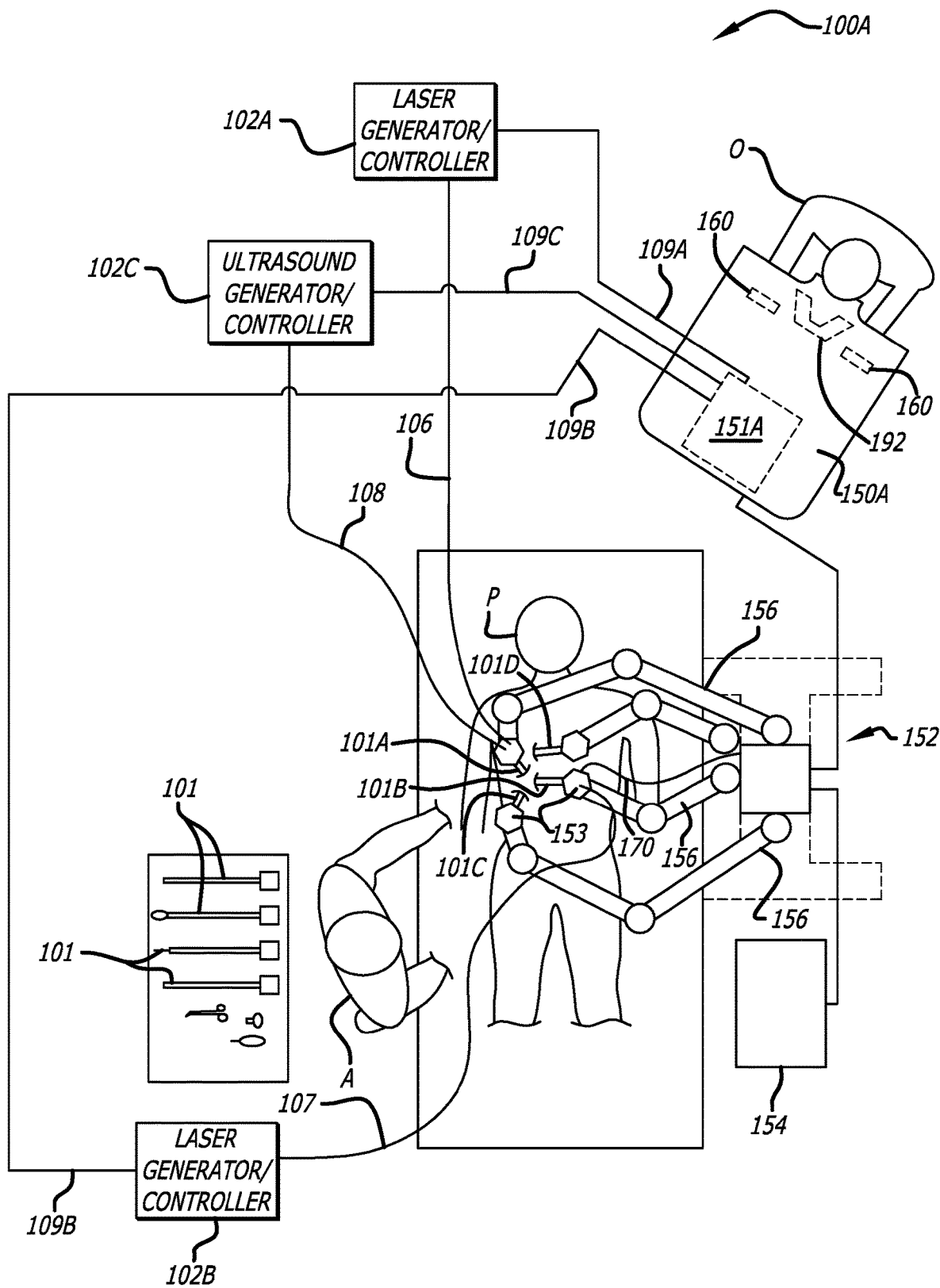
FIG. 1A is a block diagram of a robotic surgery system to perform minimally invasive robotic surgical procedures with combined laser imaging robotic surgical tools.

This detailed description describes exemplary implementations that are illustrative of the invention, and so is explanatory and not limiting. The invention is limited only by patented claims. In the drawings, some elements have been omitted to more clearly show the embodiments of the invention.

Introduction

The embodiments of the invention include an apparatus and system of robotic surgical instruments or tools used in robotic surgical systems with multiple capabilities. The robotic surgical tools include the capability to deliver laser energy for use in marking, cutting, or cauterizing tissue. A video camera, an ultrasound probe, or other imaging device is included with the robotic surgical tool to display an area of tissue in a surgical site where the laser energy may be delivered.

An end effector including both the laser and imaging device, are connected to a wristed joint capable of multiple degrees of freedom of movement. The wristed joint may use disks or vertebrae and actuation cables or tendons to allow a surgeon to remotely manipulate the end effector within small tight enclosures with a high degree of precision from a master control workstation or console. An exemplary wristed joint is described in detail in U.S. Pat. No. 6,817,974 entitled SURGICAL TOOL HAVING POSITIVELY POSITIONABLE TENDON-ACTUATED MULTI-DISK WRIST JOINT filed by Thomas G. Cooper et al. on Jun. 28, 2002 which is incorporated herein by reference.

One imaging device described in the embodiments of the invention may use an ultrasound probe to capture images of the surgical site. Ultrasonography utilizes sound waves emitted from transducers to form images. During transmit mode, acoustic energy is created by sending electrical signal to the transducer causing the elements of the transducer to resonate. The acoustic signal produced travel to nearby structures where some of the signal is absorbed and some reflected back to the transducer. In receive mode, the reverse occurs, i.e. reflected acoustic signals causes the transducer to resonate producing measurable electrical signals which can be processed into images.

The images produced by ultrasound may contain details not available to traditional laparoscopes using a light viewing scope. For example, ultrasound images may differentiate between healthy and cancerous cells based on a difference in acoustic impendence. Malignant lesions in thyroid and breast cancers are harder and stiffer than benign lesions and thus have a higher acoustic impendence that may be detectable by a trained physician or ultrasound technician.

Another image device described in the embodiments of the invention are video cameras to capture video images of the surgical site. A video camera captures images in the visible spectrum and uses a light source to illuminate the surface of tissue in a surgical site. A digital video camera with a charge-coupled device (CCD) may be used to capture digital video images of a surgical site. A bundle of optical fibers may be used as light pipes to direct a light source at one end down into the surgical site to provide the illumination to capture the digital video images. The video images captured by the camera may be transmitted to one or more viewing monitors that a surgeon uses to visualize the internal anatomy and guide any surgical procedures.

Note that while ultrasound imaging and video imaging are disclosed herein, other forms of imaging technology, such as X-ray, magnetic resonance, computed tomography, visible, infrared, and ultraviolet imaging, may also be used to display the surgical site depending on the needs of the surgeon.

Robotic Surgical System for Ultrasound Imaging and Laser Cutting

Referring for a moment to FIG. 1A, a robotic surgical system 100A is illustrated for performing ultrasound imaging and laser cutting/ablation during minimally invasive robotic assisted surgery. The robotic surgical system 100A includes one or more control workstations or surgeon's consoles 150A, a patient side manipulator or patient side cart 152, and one or more robotic surgical instruments or tools 101A-101D (generally referred to by reference number 101) coupled to the patient side cart via robotic surgical arms 153 and set up arms 156. The set up arms 156 are passive arms that are fixed into an initial position to support the robotic surgical arms. The robotic surgical arms 153 may be moved under commands from the surgeon's console to manipulate the positions of the tools 101A-101D and perform minimally invasive robotic assisted surgery.

The robotic surgical tools 101 may include such end effectors as clamps, graspers, scissors, staplers, needle holders, cameras, ultrasound imagers, and laser ablation/cutting/marking. The robotic surgical tools 101 may combine a plurality of capabilities into one tool and end effector. For example, the robotic surgical tool 101A may combine an ultrasound imaging and a laser marking capability together into one tool. As another example, the robotic surgical tool 101B may include one or more video cameras and a laser ablation/cutting capability combined into one tool. The robotic surgical tools 101C-101D may be tissue manipulation tools such as to grasp, cut, or suture tissue together, for example.

The robotic surgical tools 101 may be mounted to and dismounted from the robotic surgical arms 153 of the patient side cart 152. The patient side cart 152 is in turn coupled to the surgeon's console 150A. Commands from the surgeon's console 150A are coupled to the patient side cart 152 to generally control the robotic surgical tools 101. The robotic surgical tools 101 may send signals back to the surgeon's console 150A such that commands from the workstation 150A may be transmitted to the cart 152. To perform robotic assisted surgeries, the patient side cart 152 is positioned adjacent to a patient P as illustrated in FIG. 1A.

The robotic surgical system 100A further includes one or more laser generator/controllers 102A-102B and an ultrasound generator/controller 102C to couple to the robotic surgical tools 101A-101B to perform ultrasound imaging and laser cutting/ablation during minimally invasive robotic assisted surgery. The laser generator/controller 102A is coupled to the robotic surgical tool 101A by a cable 106. The ultrasound generator/controller 102C is coupled to the robotic surgical tool 101A by a cable 108. The laser generator/controller 102B is coupled to the robotic surgical tool 101B by a cable 107. To control the ultrasound imaging and laser cutting/ablation during minimally invasive robotic assisted surgery, the one or more laser generator/controllers 102A-102B and the ultrasound generator/controller 102C are coupled to a computer 151A in the surgeon's console 150A. The laser generator/controllers 102A-102B are respectively coupled to the computer 151A in the surgeon's console 150A by cables 109A-109B. The ultrasound generator/controller 102C is coupled to the computer 151A in the surgeon's console 150A by a cable 109C.

The power levels and wavelengths of the laser light generated by the laser generator/controllers and/or laser diodes to laser ablate/cut body tissue may vary. For example, typical power level ranges for laser ablation/cutting are (i) three to six (3-6) watt range for fine tissue dissection, not particularly wavelength dependent; (ii) ten to fifteen (10-15) watt range for larger dissections with approximately two micron wavelength; (iii) twenty-five to sixty (25-60) watt range with approximately 532 nano-meters (nm) (green light) wavelength; and (iv) up to sixty (60) watt for carbon dioxide ($CO_2$) laser (approximately ten and six tenths (10.6) micron wavelength). If the laser is to be used for marking tissue, the power level may be less, such as around one watt with approximately a two-micron wavelength.

Figure 1B:
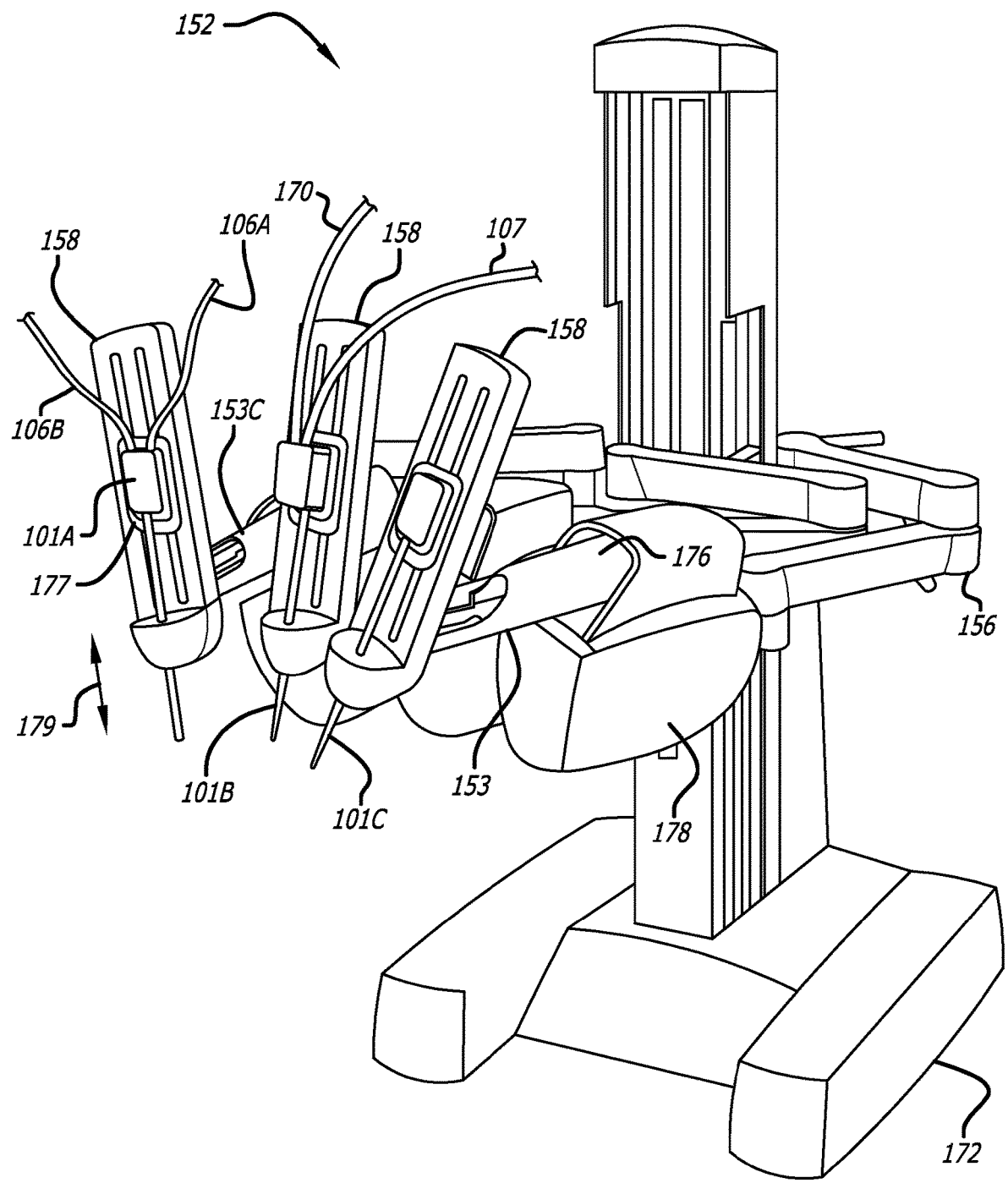
FIG. 1B a perspective view of the robotic patient-side system of FIG. 1A with combined laser imaging robotic surgical tools.

Referring now to FIG. 1B, the patient side cart 152 includes a plurality of robotic arms 153 to which the robotic surgical tools 101A-101C are removeably coupled. The interface between the robotic surgical tools 101A-101C and the robotic surgical arms 153 is the same (e.g., standardized) so that the tools are interchangeable. The movement of the robotic surgical arms 153 may be adapted to manipulate interchangeable surgical instruments, such as laser surgical tools, optical sensors, acoustic sensors, patient telemetry sensors as the need arises. Each robotic surgical arm 153 may include a sled 177 with drive mechanisms to control the position of the robotic surgical tools and the associated end effectors, if any. The sled 177 may be moved along an insertion axis parallel to the shaft of the tool as indicated by the double-headed arrow 179.

Figure 1C:
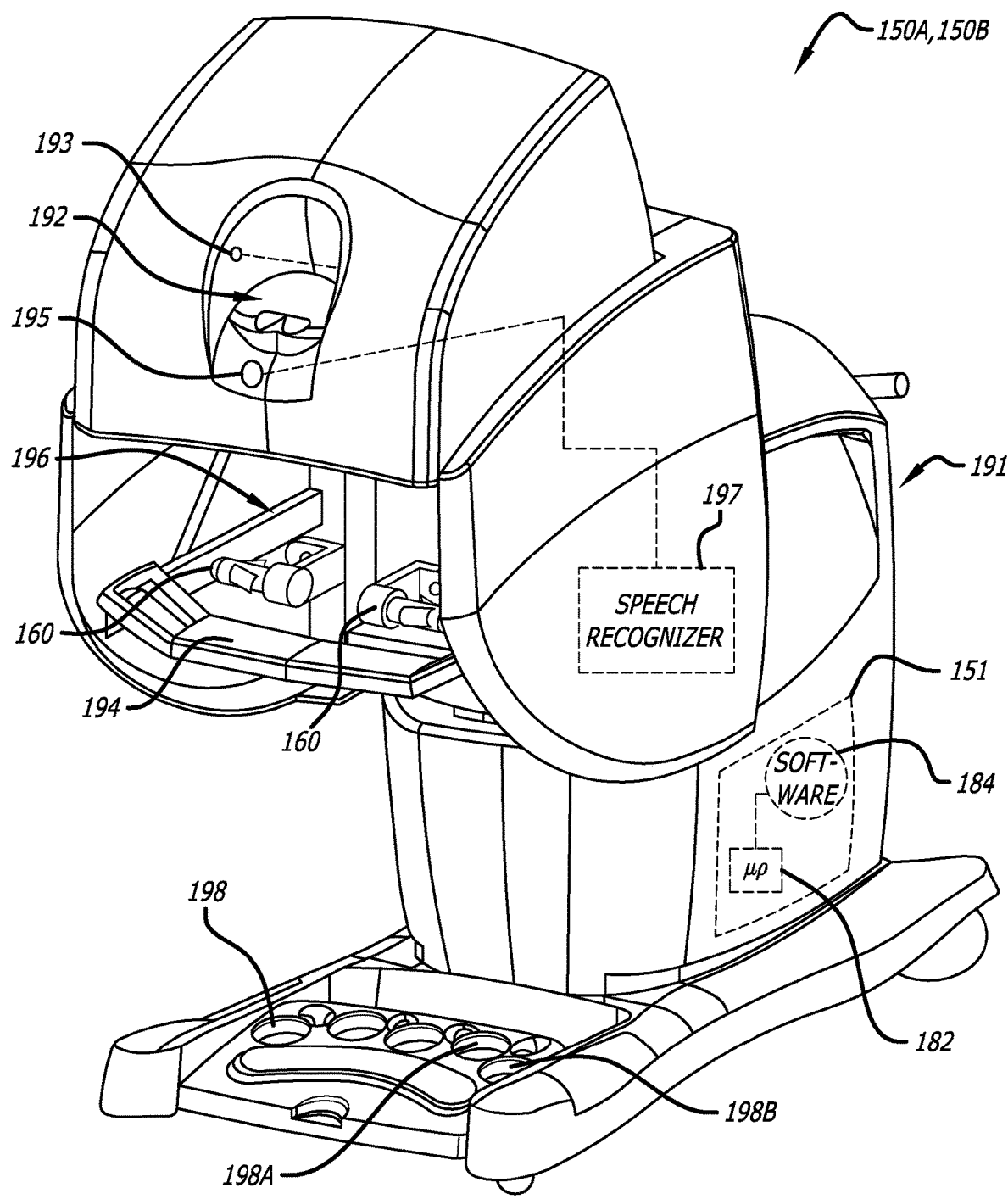
FIG. 1C is a perspective view of the robotic surgical master control console of FIG. 1A, 1D that is used to control the combined laser imaging robotic surgical tools.

Referring now to FIG. 1C, a perspective view of the robotic surgical master control console 150 is illustrated. The master control console 150 of the robotic surgical system 100 may include the computer 151, a binocular or stereo viewer 192, an arm support 194, a pair of control inputs (control input wrists and control input arms) 160 in a workspace 196, foot pedals 198 (including foot pedals 198A-198B), and a viewing sensor 193. The master control console 150 may also be referred to as a surgeon's console or workstation.

The master control console 150 provides substantial dexterity to a surgeon while working within an internal surgical site. The master control console 150 controls the motion of the servo-mechanically operated robotic surgical instruments 101. During the surgical procedure, the telesurgical system can provide mechanical actuation and control of a variety of robotic surgical instruments or tools 101 having end effectors, such as tissue graspers, needle drivers, or the like. The robotic surgical instruments or tools 101 perform various functions for the surgeon, such as holding or driving a needle, grasping a blood vessel, or dissecting tissue, or the like, in response to manipulation of the master control devices 160.

The master control console 150 allows one or more surgeons to remotely operate on a patient by providing images of the surgical site at the master control console 150. The stereo viewer 192 has two displays where stereo three-dimensional images of the surgical site may be viewed to perform minimally invasive surgery. When using the master control console, the operator O typically sits in a chair, moves his or her head into alignment with the stereo viewer 192 to view the three-dimensional images of the surgical site. To ensure that the operator is viewing the surgical site when controlling the robotic surgical tools 101, the master control console 150 may include the viewing sensor 193 disposed adjacent the binocular display 192. When the system operator aligns his or her eyes with the binocular eyepieces of the display 192 to view a stereoscopic image of the surgical worksite, the operator's head sets off the viewing sensor 193 to enable the control of the robotic surgical tools 101. When the operator's head is removed the area of the display 192, the viewing sensor 193 can disable or stop generating new control signals in response to movements of the touch sensitive handles in order to hold the state of the robotic surgical tools. While viewing a three-dimensional image of the surgical site on the stereo view 192, the surgeon performs the surgical procedures on the patient by manipulating the master input devices of the workstation.

The arm support 194 can be used to rest the elbows or forearms of the operator O (typically a surgeon) while gripping touch sensitive handles of the control input 160, one in each hand, in the workspace 196 to generate control signals. The touch sensitive handles 160 are positioned in the workspace 196 disposed beyond the arm support 194 and below the viewer 192. This allows the touch sensitive handles to be moved easily in the control space 196 in both position and orientation to generate control signals. Additionally, the operator O can use his feet to control the foot-pedals 198 to change the configuration of the surgical system and generate additional control signals to control the robotic surgical instruments.

The computer 151 may include one or microprocessors 182 to execute instructions and a storage device 184 to store software with executable instructions that may be used to generate control signals to control the robotic surgical system 100. The computer 151 with its microprocessors 182 interprets movements and actuation of the touch sensitive handles (and other inputs from the operator O or other personnel) to generate control signals to control the robotic surgical instruments 101 in the surgical worksite. In one embodiment of the invention, the computer 151 and the stereo viewer 192 map the surgical worksite into the controller workspace 196 so that it feels and appears to the operator O that the touch sensitive handles 160 are working over the surgical worksite.

The robotic surgical instruments 101A-101B on the robotic arms 158A-158B typically include elongated shafts, with proximal and distal ends. End effectors are generally mounted on wrist-like mechanisms pivotally mounted on the distal ends of the shafts, for enabling the instruments to perform one or more surgical tasks. Generally, the elongated shafts of surgical instruments allow the end effectors to be inserted through entry ports in a patient's body to access the internal surgical site. Movement of the end effectors is generally controlled via master controls on the control console 150.

Further information regarding robotic surgical systems may be found for example in U.S. Pat. No. 6,331,181, entitled SURGICAL ROBOTIC TOOLS, DATA ARCHITECTURE, AND USE, issued to Tierney et al on Dec. 18, 2001, which is incorporated by reference.

Robotic Surgical System with Remote Workstation

Figure 1D:
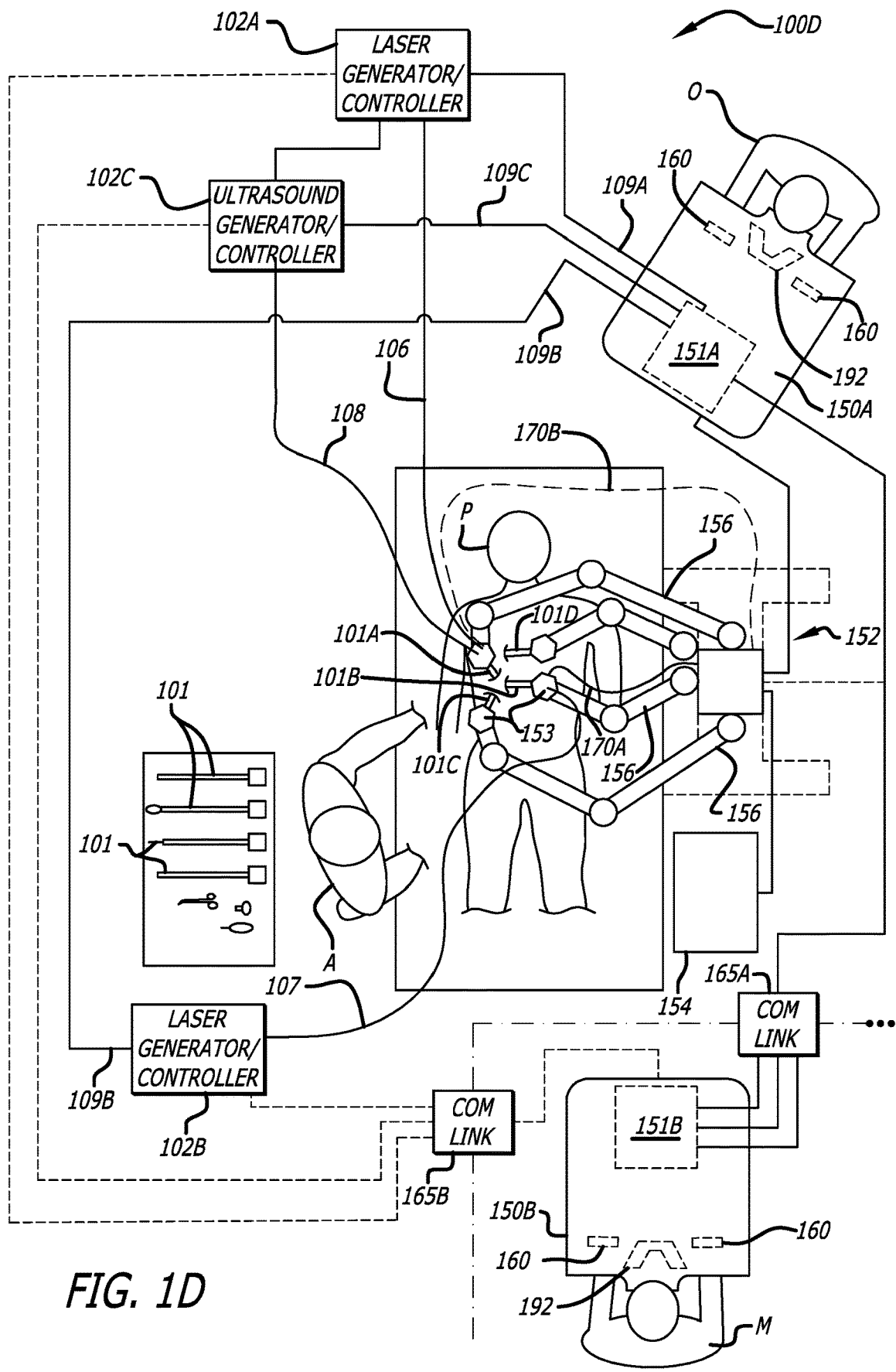
FIG. 1D is a block diagram of a robotic surgery system with multiple robotic surgical master control consoles to control the combined laser imaging robotic surgical tools.

Referring for the moment to FIG. 1D, a robotic surgical system 100D is illustrated for performing ultrasound imaging and/or laser marking/cutting/ablation during minimally invasive robotic assisted surgery. The robotic surgical system 100D differs from the robotic surgical system 100A in that a second surgeon's console 150B may also be used to control the robotic surgical tools 101 and receive signals there-from. The second workstation 150B allows another user (e.g., a second surgeon) to assist in robotic assisted surgical procedures on patients, such as if there are multiple tools being used and extra hands are needed to control those robotic surgical tools.

For example, the second surgeon's console 150B may be used to control the robotic surgical tool 101A that combines an ultrasound imaging and a laser marking capability together into one tool. A second surgeon or mentor at the second surgeon's console 150B may view ultrasound images and laser mark corresponding tissue in a body cavity for viewing by the first surgeon at the first surgeon's console 150A. Alternatively, the second surgeon at the second surgeon's console 150B may operate a laser in an end effector of a robotic surgical tool to cut or ablate tissue in a body while the first surgeon is operating other tools with his two hands.

The second surgeon's console 150B may be located remotely a distance away from the first surgeon's console 150A. The remote workstation 150B may be situated in another part of the medical facility or may be further removed and part of a greater network of remote workstations. In this case, second surgeon's console 150B may be connected as part of the surgical system through one or more communication links 165A-165B to the workstation 150A, the cart 152, and/or the generator/controllers 102A-102C.

The remote workstation 150B may be capable of indirect control of the robotic surgical tools 101 and their generator/controllers 102A-102C through the computer 151A of the workstation 150A. Optionally the remote workstation 150B may directly control the robotic surgical tools 101 and their respective generator/controllers 102A-102C.

Remote workstation 150B may have the same controls as workstation 150A including controls 160 for movement of a robotic surgical tool with an ultrasound probe and a display 192 to view images from one or more cameras and the ultrasound probe. Other controls on the surgeon console 150A and the remote workstation 150B may allow the surgeon to operate a robotic surgical tool with a laser-emitting device. The laser generator may be triggered, focused, and/or selectively powered (increase or decrease the power of the laser emitted) by using the controls on the workstation 150A or the controls of the extra workstation 150B.

For example, the robotic surgical tools 101A-101B may be combined laser-endoscopic cameras each having a camera and a laser-emitting device. Video images may be captured by the pair of cameras in the combined laser-endoscopic camera tools 101A-101B and coupled to the system via the video cables 170A-170B. Both sets of video images captured by the pair of cameras may be displayed at both surgeon consoles 150A-150B by the stereo viewer 192 of each and at the remote or assistant display 154. The laser functionality of the combined laser-endoscopic camera tools 101A-101B may be used as a laser-pointing device with a lower power laser light. The laser generator may be set to low power or the combined laser-endoscopic camera tool 101A-101B may include a low power laser diode. The mentoring surgeon M at the remote workstation 150B may control the combined laser-endoscopic camera tool 101A to point out anatomy in the patient P to the surgeon O at the local workstation 150A and those (e.g., assistant A or medical students in a remote location) watching the display 154. The operating surgeon O at the local workstation 150A may control the combined laser-endoscopic camera tool 101B to point out anatomy in the patient P to the surgeon M at the remote workstation 150A and those (e.g., assistant A or medical students in a remote location) watching the display 154. In this manner with both the operating surgeon O and the mentoring surgeon M, the may each use laser pointer devices provided by the combined laser-camera tools to discuss anatomy, such as for mentoring or proctoring.

Further information regarding a remote workstation for robotic surgical systems is found in U.S. patent application Ser. No. 11/322,866, entitled STEREO TELESTRATION FOR ROBOTIC SURGERY, filed by Ben Hambrecht et al. on Dec. 30, 2005, which is incorporated by reference.

Robotically Controlled Ultrasound Imaging and Laser Tool

Referring now to FIG. 2A, a perspective view of a combined laser-ultrasound robotic surgical tool 200A is illustrated. The combined laser-ultrasound robotic surgical tool 200A has multiple capabilities to provide ultrasound imaging and laser cutting/marking.

The combined laser-ultrasound robotic surgical tool 200A includes a mountable housing 201A, a system cable 208, a laser cable 106, a laser cable connector 210A, an ultrasound cable 108, an ultrasound cable connector 212; a hollow rotatable cylindrical shaft 214, a wristed joint 218, and a combined laser-ultrasound end effector 220 coupled together as shown in FIG. 2A. With the combined laser-ultrasound end effector 220 coupled to the wristed joint 218, the end effector 220 can be moved over multiple degrees of freedom in response to a surgeons input from the console 150A, 150B.

The mountable housing 201A includes a mountable base 204 and a housing cover 202 coupled to the base. The mountable base 204 can be mounted to and dismounted from the sled 177 (see FIG. 1B) to couple and decouple the tool 200 to/from the robotic surgical arm. This allows the tool to be quickly changed to another type of tool during surgery. Additionally, it allows the tool to be changed out for maintenance or sterilization after surgery. The mountable housing 201A includes rotatable receivers (e.g., see rotatable receivers 1310 in FIG. 13) extending from the base 204 to interface to rotatable drivers (e.g., see rotatable driver 1122 in FIG. 11) of the sled 177 and a robotic surgical arm. The rotatable receivers receive a torque to rotate the shaft 214 and to control the wristed joint 218 to move the end effector 220. Actuators coupled to the base 204 receive the torque and translate it like a transmission to actuating cables 216 to control the wristed joint 218 and move the end effector 220.

The system cable 208 coupled to the tool 200 exiting from the mountable housing 201A includes the ultrasound cable 108 and the laser cable 106. The ultrasound cable 108 further includes a plurality of ultrasound signal wires 304. The laser cable 106 may include an optical fiber for carrying laser light from a laser generator/controller (e.g., see laser generator/controllers 102A, 102B illustrated in FIG. 1B) through the tool 200 to exit out through an aperture in the end effector 220. Alternatively, the laser cable 106 may include signal wires and/or power wires to power and control a laser diode to generate the laser light in the tool 200 for exit from the aperture in the end effector 220. The laser cable connector 210A is connected to an end of the laser cable 106 to couple an end of an optical fiber or alternatively wires therein to a laser generator/controller (e.g., see laser generator/controllers 102A, 102B illustrated in FIG. 1B).

In the case of an optical fiber within the cable 106, the laser generator/controller provides the laser light of the desired wavelength and power that is coupled into the optical fiber. In the case of wires within the cable 106, the laser generator/controller provides power, ground, and control signals to control a laser diode within the tool that generates the laser light of the desired wavelength and power. In either case, the laser generator/controller is controlled by a surgeon or user at a control console 150A, 150B to generate the laser light when desired with the desired wavelength and range of power.

The ultrasound cable connector 212 is connected to an end of the ultrasound cable 108 to couple its ultrasound signal wires 304 to an ultrasound generator/controller (see ultrasound generator/controller 102C illustrated in FIG. 1B). An opposite end of the signal wires 304 in the cable 108 may couple to the ultrasound transducer elements (see ultrasound transducer elements 504 illustrated in FIGS. 5A-C) in the end effector 220. Alternatively, the opposite end of the signal wires 304 may couple to circuits to combine signals together for routing through the tool down the shaft 214 to and from the ultrasound transducer elements.

The ultrasound controller/generator 102C provides a drive signal to ultrasound transducers in the end effector 220 to cause them to emit ultrasonic energy. The ultrasound transducers in the end effector 220 further receive reflected ultrasound waves and converts them into electrical signals that are coupled back to the ultrasound generator/controller 102C for processing of the return signals received by the transducers. The ultrasound controller/generator 102C may form ultrasound images out of the return signals and provide video images over the cable 109C for display to the surgeon at the console 150A, 150B. An ultrasound controller/generator 102C and the ultrasound connector 212 are described in detail in U.S. Pat. No. 5,630,419 entitled SEALING CONNECTOR FOR MULTICONDUCTOR CABLES issued to Ranalletta, Joseph V on May 20, 1997, which is incorporated herein by reference.

The mountable housing 201A is the interface of the tool with a robotic surgical system such as the DaVinci Surgical System by Intuitive Surgical. Amongst other things, the mountable housing 201A includes the drive mechanisms or transmission under a cover 201A to move drive cables 216 which in turn move the wristed joint 218. An embodiment of the wristed joint or wrist member 218 is better illustrated by FIG. 4. The mountable housing 201A may further include an isolation chamber 203A under the cover to isolate electrical connections and cables from the drive mechanisms or transmission for the drive cables 216.

A proximal end of the hollow cylindrical shaft 214 is pivotally coupled to the base 204 of the mountable housing 201A. A proximal end of the wristed joint 218 is coupled to the distal end of the shaft 214. The end effector 220 is coupled to a distal end of the wristed joint 218. Note that the shaft 214, the joint 218, and the end effector 220 may rotate together to provide an additional freedom of movement for the end effector. The shaft 214 is a hollow cylindrical tube that extends the reach of combined laser-ultrasound end effector 220.

Figure 3:
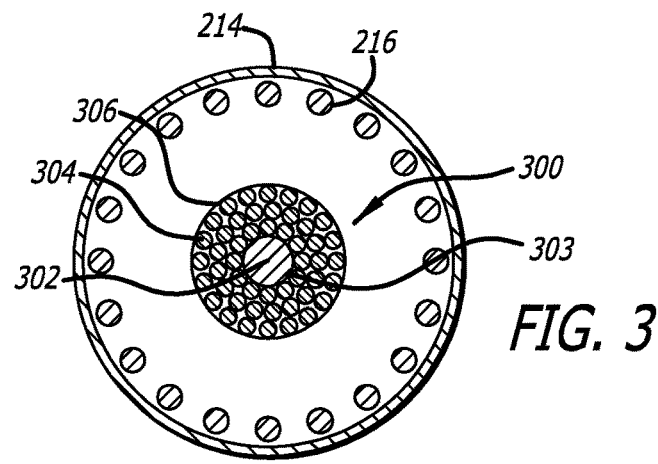
FIG. 3 is a cross sectional view of the tool shaft of the exemplary embodiments of the combined laser ultrasound robotic surgical instruments illustrated in FIGS. 2A-2B illustrating the wires and cables routed therein.

The drive cables 216 are routed within the shaft 214 and may extend over its length from the base 204 to the wristed joint 218, or extend further to an end effector. The drive cables 216 are typically arranged within the shaft to move nearer its inner surface away from a center axis of the shaft 214 as shown in FIG. 3. This provides sufficient area to route a cable bundle 300, including ultrasound signal cables 304 and a laser cable 302.

Referring now to FIG. 3, a cross section of the tool shaft 214 is illustrated to show a cable bundle 300 and drive cables 216 routed in the shaft. The cable bundle 300 is coaxially positioned near a center axis of the tool shaft 214, and is routed through the tool shaft 214, the wristed joint 218, and into the end effector 220. The cable bundle 300 includes a laser cable 302, ultrasound cables 304 around the laser cable 302, and a sheath 306 around the laser cable 302 and the ultrasound cables 304.

The drive cables 216 that are routed through the shaft 214 are spaced apart from the cable bundle 300 and positioned near the inner circumference of the shaft 214. As the drive cables 216 may move along the shaft 214, they are spaced apart from the bundle 300 to try to avoid wear. The drive cables 216 may also be spaced from each other near the inner circumference of the shaft 214 as shown. The wristed joint 218, shaft 214, and end effector 202 may include cable guides at their inner periphery to align and retain the position of the drive cables 216. Retaining the drive cables 216 on the periphery allows end effector actuation cables (if any), electrical cables, ultrasound signal wires, and optical cables, to be routed down the center or lumen of shaft 214 and wristed joint 218 with less interference.

The laser cable 302 may be in the center of the cable bundle 300, coaxially positioned near a center axis of the tool shaft 214, and run the length of the tool from the housing 201A at a proximal end to near an aperture in the end effector 220 at the distal end. In another embodiment of the invention, the laser cable 302 may further extend out from the proximal end of the tool 200A and into the laser cable 106 to couple to the laser generator/controller 102A, 102B. In one embodiment of the invention, the laser cable 302 is a fiber optic cable, light pipe, or optical fiber to propagate the laser energy generated by a laser diode (e.g., laser diode 708 in FIG. 7A) or the laser controller/generator 102C through the tool 200A, 200B to exit from an aperture in the end effector 220. In another embodiment of the invention, the laser cable 302 is one or more electrical cables to power and control a laser diode (e.g., laser diode 608 in FIG. 6B) in the end effector 220 so that the laser energy is locally generated by the tool.

The ultrasound signal wires 304 in the bundle 300 near the laser cable 302 are numerous. The number of ultrasound signal wires 304 and relative size of the cables shown in FIG. 3 are for illustration purposes only. The actual number of ultrasound signal wires 304 within the cable bundle 300 depends upon the capabilities of the ultrasound probe and the number of ultrasound transducer elements. The greater the number of ultrasound transducer elements, the greater is the number of ultrasound signal wires 304 routed in the cable bundle 300. The ultrasound signal wires 304 are insulated electrical cables for driving signals to excite the ultrasound transducer elements to generate the ultrasound waves and for receiving return signals back from the ultrasound transducer elements for coupling to an ultrasound controller/generator for signal processing.

In one embodiment of the invention, the ultrasound transducer 500 includes one hundred twenty eight (128) ultrasound transducer elements 504 arranged along the length of the ultrasound probe 500. The acoustic window 510 may be one (1) transducer element wide and one-hundred-twenty-eight (128) transducer elements in length. In this case, the 128 transducers elements require 128 cables with two wires in each to drive them or more specifically, 256 conductors. Each transducer element typically has a pair of wires, a signal wire and a ground wire. The signal wire is for both transmitting and receiving ultrasound signals.

The sheath 306 is provided around the laser cable 302 and the ultrasound cables 304 to protect and bundle them together. The cable sheath 306 may comprise one or more segments of different material depending upon the location of the cable bundle within the tool. The one or more segments of the cable sheath 306 may be made of a flexible material or a rigid material. For example, the segment of the cable sheath 306 in the tool shaft 214 may be a rigid insulating plastic if the tool shaft itself is rigid. In contrast, the segment of the cable sheath 306 in the wristed joint is a flexible material. Otherwise, a rigid sheath may limit the movement of the end effector 202. One of the purposes of the cable sheath 306 is to protect the ultrasound signal wires 304 and the laser cable 302 from contact with the drive cables 216. Although the drive cables 216 may be routed through guide holes, slackening and tensioning of the drive cables 216, as well as movement of the bundle 300, may result in inadvertent contact of the sheath 306 with the drive cables.

The cable sheath 306 may also facilitate the removal and replacement of the laser cable 302 contained therein. The cable sheath 306 may facilitate catherizing the laser cable 302 so that it may be removed and replaced in case of a malfunction. The cable sheath 306 may provide a guide for threading the laser cable 302 through the tool shaft 214 and the wristed joint 218 with minimal interference from the drive cables 216.

Figure 4:
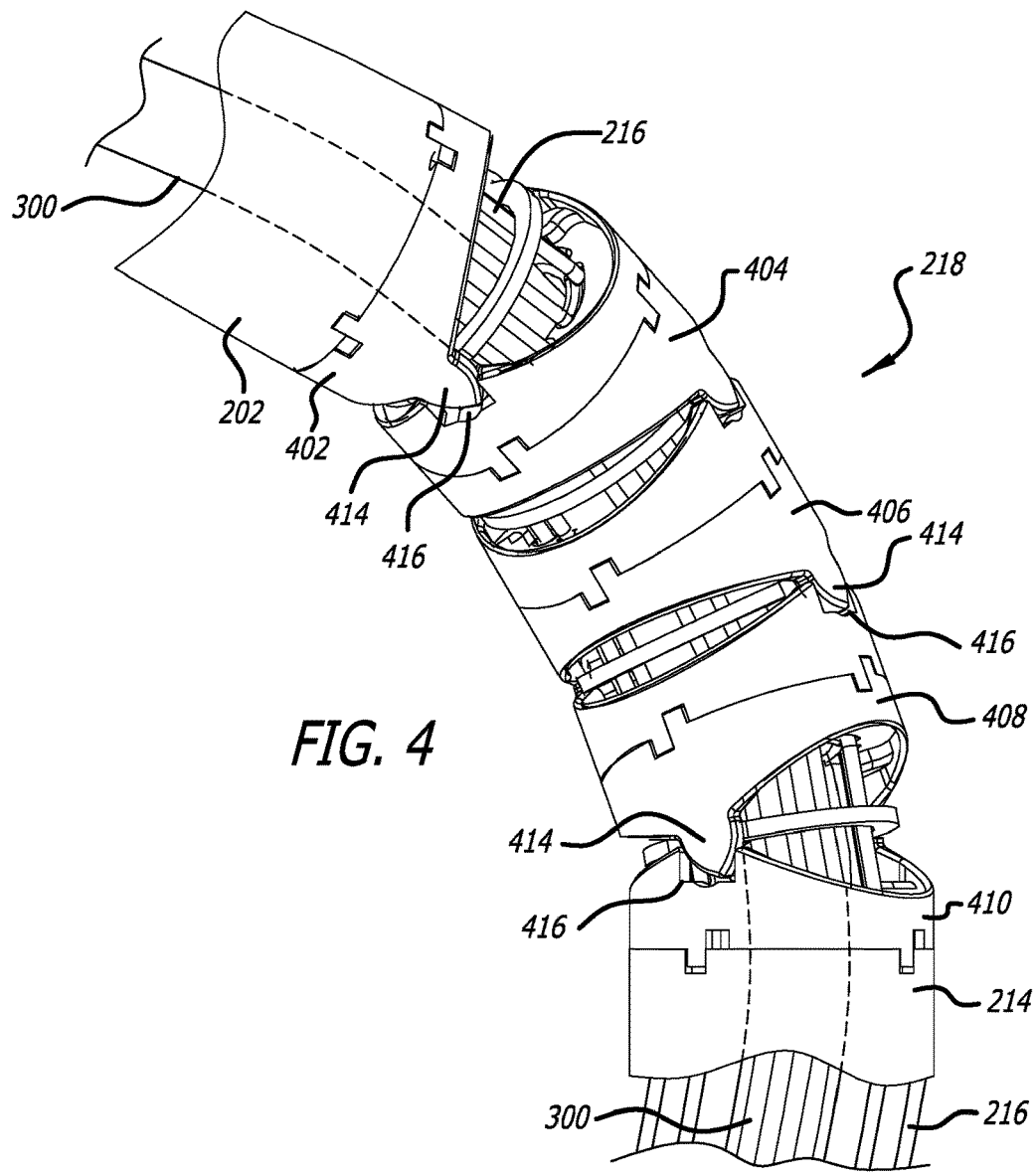
FIG. 4 is a magnified side view of the wristed portion of the exemplary embodiments of combined laser ultrasound robotic surgical instruments illustrated in FIGS. 2A-2B.

Referring now to FIG. 4, the cable bundle 300 is routed through the wristed joint 218 to the end effector 220. The wristed joint seeks to emulate the dexterity of a surgeon's wrist in the tool 200A, 200B. The wristed joint 218 is used to manipulate the position of the combined laser imaging end effector 202 over at least two degrees of freedom. Other end effectors or working elements may be combined together and coupled to the wristed joint to perform robotic assisted surgery such as scissors, graspers, scalpels, or imaging devices such as high definition optical cameras and ultrasound probes. A wide range of motion in the wristed joint 218 is especially advantageous in a small surgical site to position the end effector 220 therein.

In one embodiment of the invention, the wristed joint 218 is a segmented wrist joint and includes a plurality of hollow disks or vertebrae 402-420 stacked or coupled in a series between the end effector 202 and the shaft 214. A proximal vertebra 410 is coupled to the shaft 214. A distal vertebra 402 couples to and supports the end effector 202. The distal vertebra 402 may serve as a mounting base for various kinds of single-element and multi-element end effectors, such as scalpels, forceps, scissors, cautery tools, retractors, and the like. There is at least one intermediate or medial vertebra 404-408 disposed between the proximal vertebra 410 and the distal vertebra 402 to provide at least two degrees of freedom. Each disk or vertebrae 402-410 is configured to rotate in at least one degree of freedom with respect to each neighboring disk. In one embodiment of the wristed joint, a pair of tabs or segments 414 on opposite sides of the distal vertebra 402 and the intermediate vertebra 404-408 pivotally interface with a pair of slots 416 on opposite sides of the intermediate vertebra 404-408 and the proximal vertebra 410 for the wristed joint to pivot in a controlled manner.

A central lumen internal to the hollow disks or vertebrae 402-420 may serve as a conduit for fluid conduits (e.g., laser cooling, gas blower, irrigation, or suction), and the cable bundle 300.

The plurality of drive cables 216 routed in the shaft 214 extend into the wristed joint 218. The drive cables 216 may be one or more cable loops. One or more drive cables 216 may extend through the wristed joint 218 and into the end effector to actuate working elements. A distal portion of the drive cables 216 actuating the wristed joint 218, are generally coupled to one or more of the plurality of hollow disks or vertebrae 402-420 to pivotally actuate the connected vertebra. A proximal portion of the drive cables 216 ends within the mountable housing 201A, 201B of the tool 200A, 200B. The proximal portion of drive cables 412 actuating the wristed joint 218 may generally be coupled to drive mechanisms within the mountable housing 201A. The drive mechanisms within the mountable housing are configured to controllably move at least selected ones of the plurality of drive cables 216 to pivotally actuate the plurality of connected vertebrae 402-410 to bend the wrist member with respect to the shaft.

This and alternate embodiments of a segmented wrist joint for the wristed joint 218 are more fully described in U.S. Pat. No. 6,817,974 entitled SURGICAL TOOL HAVING POSITIVELY POSITIONABLE TENDON-ACTUATED MULTI-DISK WRIST JOINT filed by Thomas G. Cooper et al. on Jun. 28, 2002, which is incorporated herein by reference.

Referring now to FIGS. 3 and 4, the cable bundle 300 is routed through the wristed joint 218 to the end effector 220. The cable bundle 300 is positioned towards the center portion of the wristed joint 218 to avoid the vertebrae and drive cables 216 and to minimize bending of the cable bundle 300 therein. The cable sheath 306 of the cable bundle 300 further protects the ultrasound cables 304 and the laser cable 302 from the vertebrae of the wristed joint and the drive cables.

It may be preferable to retain the laser cable 302 near the center of the bundle 300. In one embodiment of the invention, the laser cable 302 is an optical fiber. The placement of the cable bundle 300 near the center of wristed joint 218 may limit damage to an optical fiber by insulating it in several layers of cables 304 and the sheath 306. If an optical fiber is overly bent greater than a predetermined angle, the optical signal within the cable may refract and escape through the fiber cladding thereby lowering the laser energy that may be propagated therein. Excessive bending may also permanently damage an optical fiber by causing micro cracks therein that may compromise light transmission. This may result is bend loss in an optical fiber such that there is a loss of signal strength from one end of the fiber to the other. The center of the shaft and wristed joint may experience less bending than the periphery. Thus, placement of the laser cable 302 near the center of the cable bundle may subject an optical fiber to less bending relative to the outer circumference of the wristed joint 218. Retaining the optical fiber near the center of the wristed joint and cable bundle 300 insulated by the outer layers of cables, wires, and sheathing surrounding it, may help limit the bending and shock an optical fiber may experience. To ease replacement in the case of damage, the laser cable 302 may have its own sheath or conduit 303 into which the cable may be removed and inserted for replacement purposes.

Referring now to FIGS. 5A-5C, views of alternate embodiments 220A-220C of the combined laser ultrasound imaging end effector 220 are illustrated. Each of the embodiments of the combined laser ultrasound imaging end effectors 220A-220C includes an ultrasound probe 500 to provide ultrasound images and facilitate laser marking/cutting by laser. Each of the end effectors 220A-220C couples to the wristed joint 218 and includes a case, housing, or enclosure 502; a plurality of ultrasound transducer elements 504 forming the ultrasound probe 500; and an opening or aperture 506 from which laser light may exit for marking or cutting. The laser cable 302 from the wristed joint 218 is routed towards the laser aperture 506 in each. The ultrasound cables 304 from the wristed joint 218 are routed and coupled to some of the plurality of ultrasound transducer elements 504 of the ultrasound probe 500.

The laser aperture 506 may be located in different positions as illustrated by the embodiments of the combined laser ultrasound imaging end effectors 220A-220C of FIGS. 5A-5C, respectively, so as to minimize interference with the ultrasound acoustics of the ultrasound transducer elements 504. For example, in FIG. 5A, the laser aperture 506 is longitudinally positioned near a mid region of the ultrasound probe 500 and the edge of the enclosure 502 so as to avoid a break in the ultrasound transducer elements. In FIG. 5B, the laser aperture 506 is positioned near a distal end of the ultrasound probe 500 and a center of the enclosure 502. In FIG. 5C, the laser aperture 506 is positioned near a proximal end of the ultrasound probe 500 and a center of the enclosure 502.

The enclosure 502 is a protective case surrounding the plurality of ultrasound transducer elements 504 of the ultrasound probe 500. The enclosure 502 may be hermetically sealed so that body fluids such as gastric juices, blood, bile, etc. are not trapped in its interior. This is so the tool 200A, 200B may be readily sterilized for repeated use in different robotically assisted surgeries of different patients. The enclosure 502 can also protect the ultrasound probe 500 during sterilization procedures.

The enclosure 502 is typically formed of an acoustically appropriate material to provide an acoustic lens or window 510 for the ultrasound transducer elements 504 of the ultrasound probe 500. A separate acoustic lens or window 510 over the ultrasound transducer elements 504 may be hermetically sealed to the housing. In which case, the enclosure 502 may be made of a different material that is not as acoustically appropriate as the window 510. In one embodiment of the invention, the non-acoustic portions of the housing or enclosure 502 are formed of ULTEM 1000 polyetherimide (generally, an amorphous polymer or plastic) made by General Electric Company, for example, while the acoustic lens or window 510 is formed out of an acoustically acceptable material, such as a silicone room temperature vulcanizing (RTV) compound made by Dow-Corning, for example. Alternatively, the entire housing or enclosure 502 may be made of the same material as the acoustic lens or window 510. For injection molding of the casing and lens as one-piece, it may be desirable to cast the entire enclosure 502 out of silicone room temperature vulcanizing (RTV) compound. When using a casing material having non-acoustic properties, the ultrasound lens or window 510 can be formed separately from other suitable acoustic materials, such as polyurethanes for example.

The internal structure of the enclosure 502 may be formed of a rigid material. Because autoclaving is an often used disinfecting/sterilization method the deformation temperature of the internal structures should also exceed the 249 degrees Fahrenheit of typical autoclave procedures. By way of example, metals such as aluminum, stainless steel, brass, or even structural plastic may be used. The internal structure of the enclosure 502 may have receptacles to receive the array of ultrasound transducers 504, as well as channels in which the laser cable 302 and ultrasound signal wires 304 may be routed from the wristed joint 218.

The ultrasound probe 500 transmits acoustic energy into body tissue within a surgical site and converts the return signal into an electrical signal. The ultrasound transducer elements 504 of the ultrasound probe 500 transmit an acoustic signal into the body tissue of a patient. The signal bends when it encounters the interfaces between different structures, i.e. when it encounters material with a different acoustic impendence, and is reflected back. The reflected signal is received by the ultrasound transducer elements 504 and processed into an image of the surgical site.

The intensity of the return signal and the time it takes to receive the signal may be plotted by a computer processor to produce a two dimensional image of the area scanned by the ultrasound probe 500. Generally the closer the probe 500 is to the tissue or organ being scanned, the better the resolution of the ultrasound image. To produce three-dimensional images with the ultrasound probe 500, multiple arrays of transducers 504 are used or alternatively the probe 500 may be rotated or moved around to scan tissue or organs from different positions to generate multiple images. The multiple images may then be combined together and interpolated by computer software to display three-dimensional images.

The transducer elements 504 comprise piezoelectric ceramic elements. In order to resonate the piezoelectric ceramic element and receive a return signal, each is electrically connected to a signal source and ground. The transducer elements 504 may be arranged into a one-dimensional array or a multi-dimensional array.

The series of piezoelectric ceramic elements, which make up transducer elements 504, may be formed out of a single piece of ceramic material. A break in the series of transducer elements 504 to incorporate the laser aperture 506 may be impractical. Furthermore, a laser aperture 506 placed amongst the transducer elements 504 may distort the return signal. By positioning the laser aperture 506 to the side or the ends of the ultrasound probe 500 without breaking up the transducer elements 504, problems may be alleviated or avoided. Thus, the position of the laser aperture 506 is made outside the ultrasound probe 500 in FIGS. 5A-5C to try to minimize interference with the ultrasound signals.

Further description of the transducer elements 504 and their formation into the ultrasound probe 500 may be found in U.S. Pat. No. 6,088,894 entitled METHODS OF MAKING COMPOSITE ULTRASONIC TRANSDUCERS issued on Jul. 18, 2000 to inventors Oakley et al., which is incorporated herein by reference.

Figure 6A:
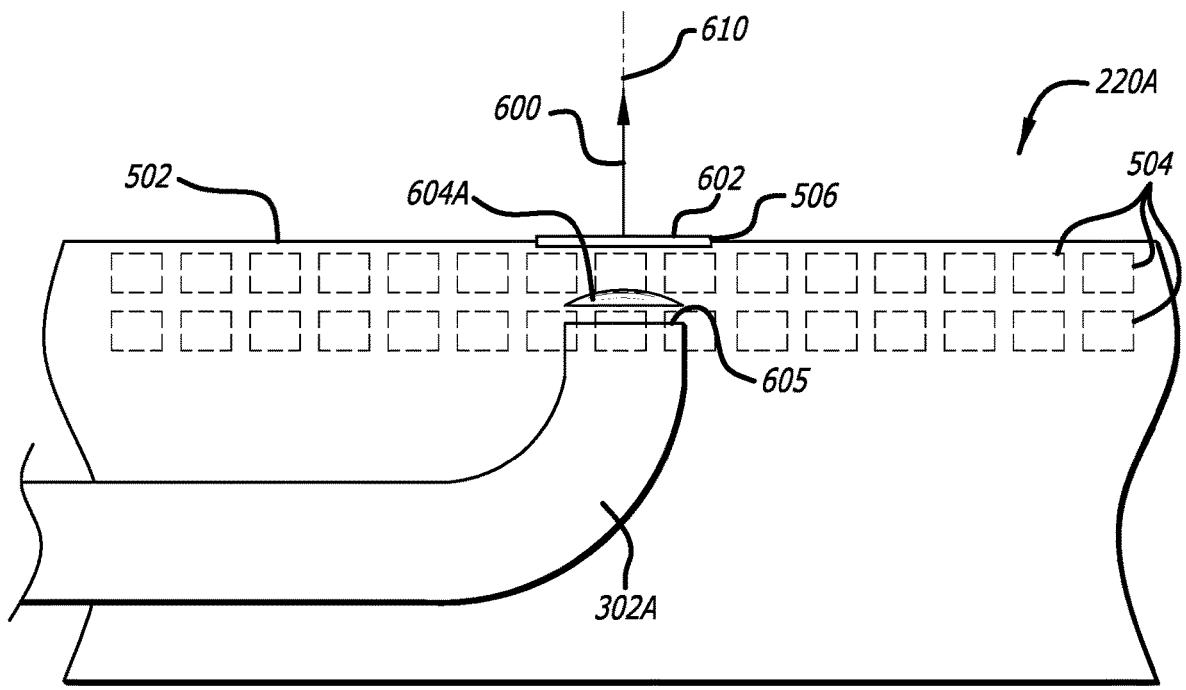
FIGS. 6A-6B are magnified cutaway side views of exemplary embodiments of the combined laser and ultrasound end effector.
Figure 6B:
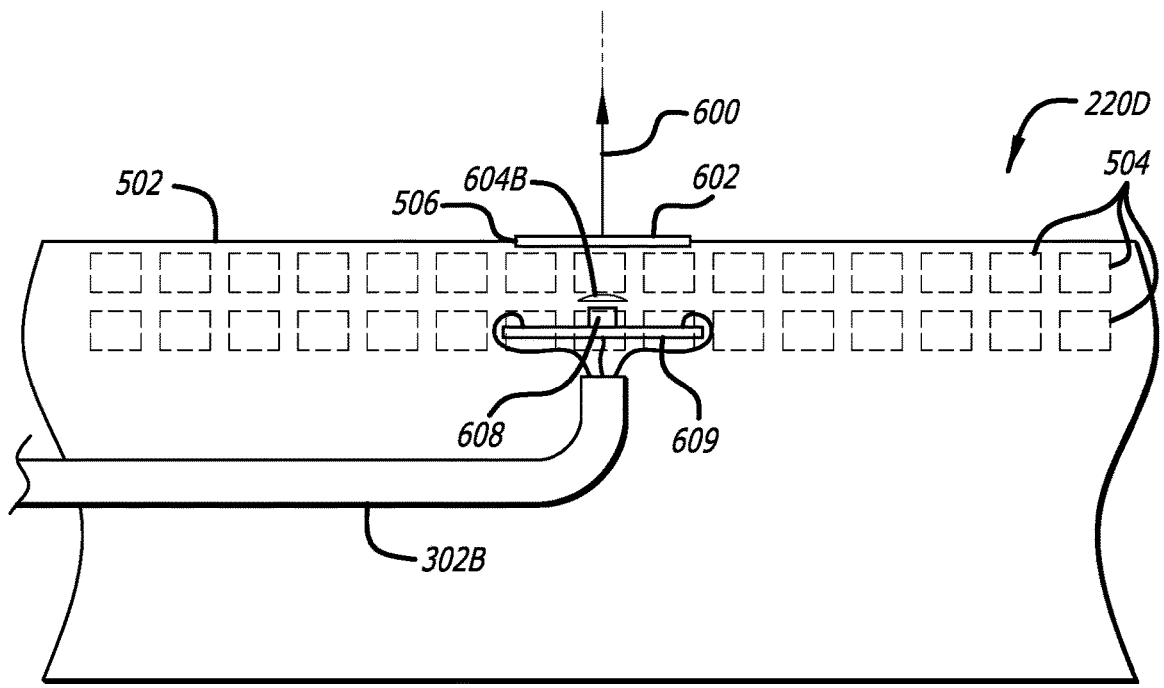

Referring now to FIGS. 6A-6B, alternate embodiments of transmission and generation of laser energy in the end effector 220 are illustrated. The laser cable 302 in the cable bundle 300 may be an optical fiber 302A as shown in FIG. 6A or one or more electrical cables 302B as shown in FIG. 6B. In either case, photons of a laser light 600 may exit out from the aperture 506 in the enclosure 502. The position of the aperture 506 in the end effector is chose to minimize interference to the individual piezoelectric transducer elements 504 that are stacked in series to form the ultrasound probe 500.

The end effector 220 may have a lens or a transparent cover 602 mounted and hermetically sealed into the aperture 506. The lens or transparent cover 602 may provide additional collimation or focusing of the laser light. Alternatively, a separate collimating or focusing lens 604A,604B may be provided under the transparent cover 602 to further collimate or focus the laser light prior to it exiting out from the end effector though the aperture 506. The transparent cover 602 and lens 604A,604B are aligned with the optical axis 610 of the laser light 600.

The transparent cover 602 may be flat-shaped and level with the surface of the ultrasound probe enclosure 502 to be cleaned more easily and thoroughly than a curved lens. The transparent cover 602 may be made of a scratch resistant transparent plastic, fiberglass, glass, crystal, or Plexiglas material suitable for transmitting the wavelength of the laser light through it. The transparent cover 602 may be hermetically sealed to the enclosure 502 of the end effector to avoid the intrusion of contaminants into ultrasound probe 500. With a hermetic seal around the transparent cover, liquid and gaseous disinfectants that may be used to clean the end effector after surgery is prevented from entering the enclosure 502 and damaging the piezoelectric elements and electrical connections made therein. If scratched or otherwise damaged the transparent cover 602 may easier to replace than a curved lens 604A,604B.

Light emitted from the distal end 605 of fiber 302A diverges in angle, by an amount determined by the angular spread of the light entering the proximal end of the fiber. In order to couple the laser light into the smallest possible fiber core, the laser source may use focusing optics to couple the light, which results in a significant angular divergence of the entering beam, and therefore of the exiting beam as well. In addition, laser light traveling through the insufflating gas used in laparoscopic surgery may excite the gas and cause it to act as a defocusing lens. When a laser is defocused the diameter of the laser dot increases without a corresponding increase in the power, thus causing a loss of power density. This blooming effect may cause the laser to char and coagulate instead of cutting tissue as desired. To maintain the highest possible power density at the outer surface of transparent window or cover 602, which with an ultrasound instrument is in contact with the tissue, a converging lens or lens system may be used, illustrated schematically in FIG. 6A by a single plano-convex lens 604A.

In FIG. 6A, laser energy generated by an external laser generator (e.g., laser controller generator 102C of FIG. 1A) or a remote internal laser diode (e.g., laser diode 708 of FIG. 7A) travels down the optical fiber 302A and is launched out the end of the optical fiber 302A parallel to the optical axis 610. The collimating lens 604A may also collimate the laser light launched out of the end of the optical fiber 302A so it is substantially parallel to the optical axis 610. The collimated laser light may exit out of the end effector through the transparent cover 602 and onto targeted tissue in a patient's body.

The optical fiber 302A may be a flexible fiber optic cable for carbon-dioxide ($CO_2$) lasers produced by OMNIGUIDE, for example, if a $CO_2$ laser is used in the laser controller/generator.

In FIG. 6B, the end effector 220D includes a laser diode 608 coupled to a printed circuit board (PCB) 609 that is mounted in the housing under the aperture 506. The one or more electrical cables 302B couple to the printed circuit board 609 in electrical communication with the laser diode 608. The active region of the laser diode 608 is centered in alignment with the optical axis 600 under the cover 602 and the lens 604B. In this case, the laser energy is locally generated by the tool to ease the cable connections to the tool.

The laser diode is excited by power and signals from the electrical cables 302B to generate photons of sufficient energy to exit the active region of the laser diode. The photons or laser light from the laser diode, being somewhat parallel to the optical axis 610 but still diverging from the emitting area of the laser diode, is coupled into the lens 604B. The focusing lens 604B may collimate the laser light launched out of the laser diode so it is substantially parallel to the optical axis 610, or focus it at a desired distance from the lens 604B, to control the location along the optical axis 610 where the maximum power density is attained. The collimated laser light may exit out of the end effector 220D through the transparent cover 602 and onto targeted tissue in a patient's body.

If the laser diode 608 is being used to mark tissue at lower laser power levels, cooling the laser diode may be unnecessary. However, if the laser diode is being used to cut or ablate tissue at higher power levels, cooling the laser diode may be useful. If so, a heat sink (not shown) may be thermally coupled to the laser diode to draw heat away from it. Alternatively, a liquid cooling may be provided from an auxiliary channel (not shown) by flowing an irrigating liquid (e.g., sterile water or saline) pass the laser diode 608 and out of the tool to provide irrigation in the surgical site and perhaps a backstop to the laser light. The heat transfer may be by convection or by directly leaking some of the irrigating liquid around the laser diode avoiding obscuring the surgical site but sufficient to cool the laser.

Figure 7A:
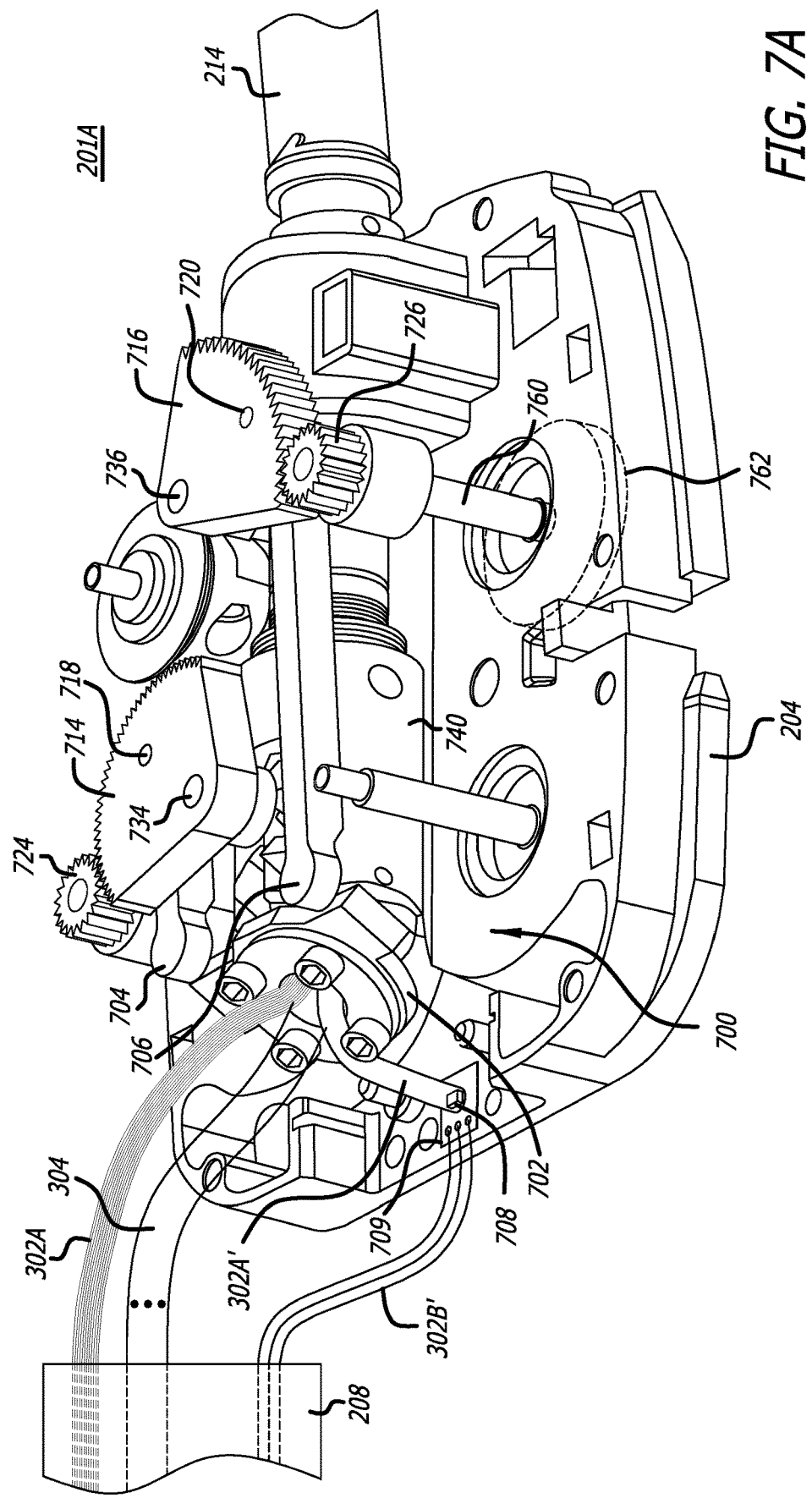
FIGS. 7A-7B are perspective views of a proximal end of exemplary robotic surgical tools with covers removed to show the cabling and connectors for the laser and ultrasound end effectors.

Referring now to FIG. 7A, the mountable housing 201A of the tool 200A is illustrated with its cover 202A removed to show the internal drive mechanisms and cable connections. The mountable housing 201A includes a gimbaled cable actuator 700 to manipulate the cables to control movement of the wristed joint 218. The actuator 700 includes a rocker or actuator plate 702 mounted in a gimbaled configuration. The actuator plate 702 pivotally coupled to a parallel linkage 740. An articulated parallel strut/ball joint assembly is employed to provide a gimbaled support for the actuator plate 702. This allows the actuator plate 702 to tilt in two degrees of freedom.

The proximal ends of the drive cables 216 are coupled to the actuator plate 702 to control the movement of the wristed joint 218. Apertures on the actuator plate 702 receive the proximal end of the drive cables 216 that extend to the disks or vertebrae of the wristed joint 218.

The actuator 700 further includes a first actuator link 704 and a second actuator link 706 are rotatably coupled near one end to the actuator plate 702 through ball joint mechanisms. The actuator plate 702 is moved by the first actuator link 704 and the second actuator link 706 to produce pitch and yaw rotations in the wristed joint 218.

The actuator 700 further includes a first follower gear quadrant 714 and a second follower gear quadrant 716 pivotally coupled to the mountable base 204 at pivot points 734 and 736, respectively. The first follower gear quadrant 714 is pivotally coupled to the first actuator link 704 near its second end by a pivot joint 718. The second follower gear quadrant 716 is pivotally coupled to the second actuator link 706 near its second end by a pivot joint 720.

The actuator 700 further includes a first drive gear 724 and a second drive gear 726 geared to the first follower gear quadrant 714 and a second follower gear quadrant 716. Each of the first drive gear 724 and the second drive gear 726 are coupled to a first end of a rotatable drive shaft 740 extending through the mountable base 204. A rotatable receiver 742 is coupled to the opposite end of each rotatable drive shaft 740. Each rotatable receiver 742 of the tool mates with a rotatable driver of the robotic surgical arm when mounted thereto.

As the rotatable receivers 742 are driven by a rotatable driver of the robotic surgical arm, the drive gears 724,726 rotate to respectively pivot the first and second follower gear quadrants 714, 716 about their respective pivot points 734, 736. As the first and second follower gear quadrants 714, 716 rotate about their respective pivot points 734,736, the actuator links 704, 706 coupled by the joints 718,720 to the gear quadrants are driven to generally move longitudinally and pivot the actuator plate 702 and move the drive cables 216.

FIG. 7A illustrates the actuator plate 702 of the gimbaled cable actuator 700 in a pitch rotation by both actuator links 704, 706 moving together in parallel. A mixture of pitch and yaw rotations in the actuator plate 700 is the result of mixed movement in the actuator links 704, 706 in response to the corresponding rotation of the rotatable receivers 742, rotatable drive shafts 740, and gears 724,726.

The cable actuator 700 is described in further detail in U.S. Pat. No. 6,817,974 entitled SURGICAL TOOL HAVING POSITIVELY POSITIONABLE TENDON-ACTUATED MULTI-DISK WRIST JOINT filed by Thomas G. Cooper et al. on Jun. 28, 2002, which is incorporated herein by reference.

However, alternative embodiments of the pivoted-plate cable actuator mechanism having aspects of the invention may have different structures and arrangements for supporting and controllably moving the actuator plate 702. For example the plate may be supported and moved by various types of mechanisms and articulated linkages to permit at least tilting motion in two DOF, for example a Stewart platform and the like. The plate assembly may be controllably actuated by a variety of alternative drive mechanisms, such as motor-driven linkages, hydraulic actuators; electromechanical actuators, linear motors, magnetically coupled drives and the like.

In one embodiment of the invention, an optical fiber 302A is routed from the aperture 506 at the end effector through the tool 200A into the cable 106 to the connector 210A as shown in FIGS. 2A, 3, 4, 5A, 6A, and 7A. In this case, an external laser generator/controller (e.g., laser generator/controller 102A of FIG. 1A) is used to generate the laser light.

In another embodiment of the invention, an optical fiber 302A is routed from the aperture 506 at the end effector 202 through the shaft 214 and to a laser diode 708 coupled to a printed circuit board 709 mounted in the housing 201A. An end of electrical laser cables 302B' are coupled to the printed circuit board 709 in communication with the laser diode 708. The electrical laser cables 302B' are routed in the laser cable 106 and couple to the connector 210A. Instead of generating the laser light, the laser generator/controller 102A generates control signals in the electrical laser cables 302B' to control the local generation of laser light by the laser diode 708. The laser light generated by the laser diode 708 is coupled into the optical fiber 302A' to route the laser light through the tool to the aperture 506 in the end effector 220.

Figure 2B:
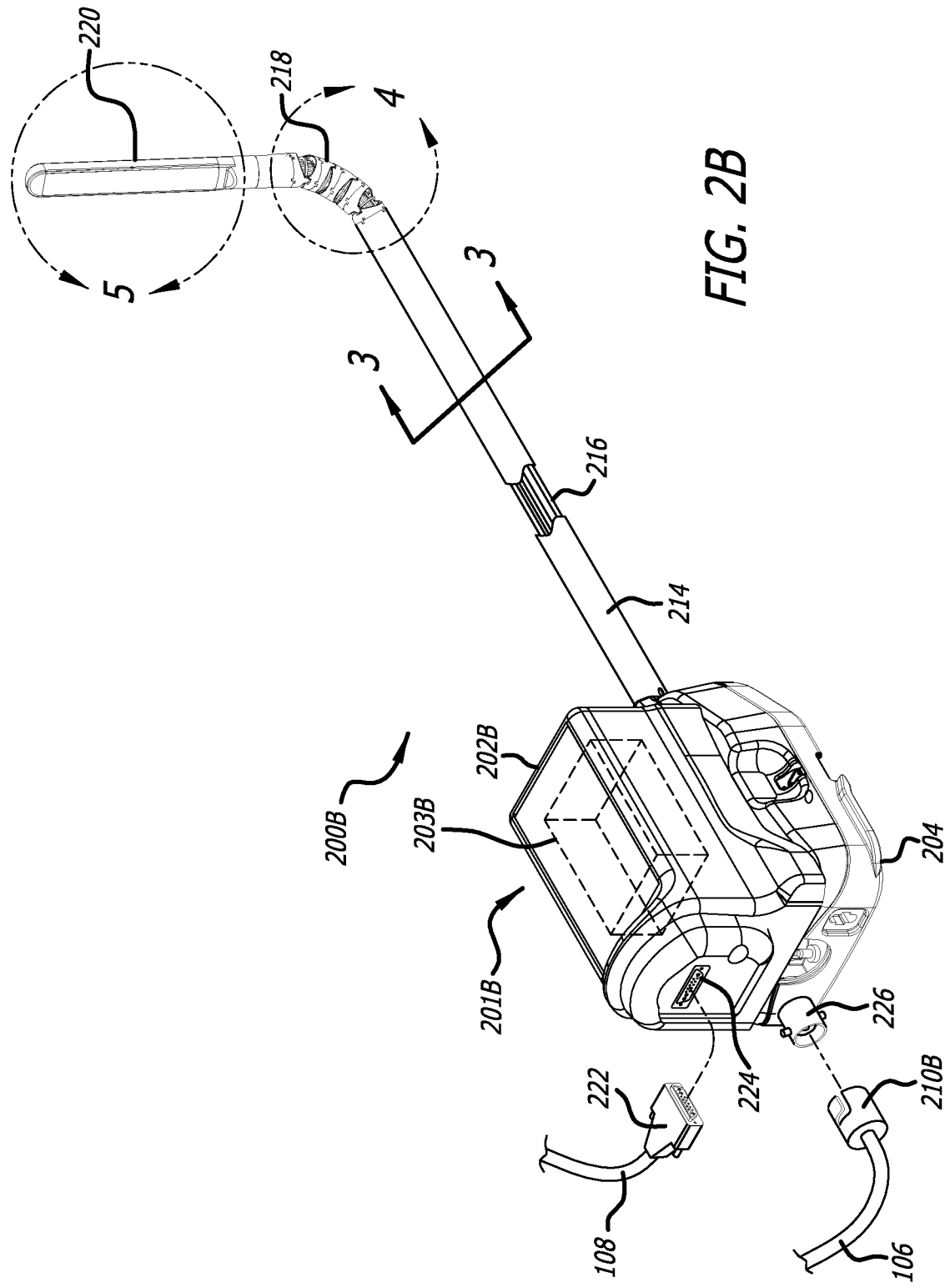

Referring now to FIG. 2B, an alternate embodiment of a combined laser imaging tool 200B is illustrated. The combined laser imaging tool 200B is similar to the combined laser imaging tool 200A but generally differs in the mountable housing 201B and how a laser cable 106 and an ultrasound cable 108 couple there-to. The laser cable 106 provides a means for routing signals from a laser generator/controller to the robotic surgical tool 200B. The ultrasound cable 108 provides a means for routing signals from an ultrasound generator/controller to the robotic surgical tool 200B. With the combined laser imaging tool 200B, the laser cable 106 and the ultrasound cable 108 are readily detachable from the tool. This may be advantageous to ease sterilizing the tool or to more quickly make equipment changes.

Referring for the moment to FIG. 2A, a first laser cable connector 210A is coupled to a first end of the laser cable 106 as shown. The first connector 210A is used to connect the laser cable 106 to a laser generator/controller. Referring now to back FIG. 2B, a second laser cable connector 210B is coupled to the second end of the laser cable 106. To connect the laser cable 106 to the tool 200B, the second connector 210B quickly couples to a laser cable receptacle 226. The second connector 210B may also be quickly detached from the receptacle 226. The first and second connectors 210A-210B may be male bayonet Neill-Concelman (BNC) connectors and the receptacle 226 may be a female BNC connector. If a surgeon decides a different robotic surgical tool is needed in place of the tool 200B, the cable 106 can be quickly detached to more quickly make a tool change.

Referring for the moment to FIG. 2A, a first ultrasound connector 212 is coupled to a first end of the ultrasound cable 108 as shown. The first connector 212 is used to connect the ultrasound cable 108 to an ultrasound generator/controller. Referring now to back FIG. 2B, a second ultrasound connector 222 is coupled to the second end of the ultrasound cable 108. To connect the ultrasound cable 108 to the tool 200B, the second connector 222 quickly couples to an ultrasound receptacle 224. The connector 222 may be a male electrical pin connector while the receptacle 224 is a female electrical pin connector. The second connector 222 may be quickly detached from the receptacle 224. If a surgeon decides a different robotic surgical tool is needed in place of the tool 200B, the cable 108 can be quickly detached to more quickly make the tool change.

The ultrasound wires 304 coupled to the ultrasound transducers 504 may couple to the receptacle 224. However, with the electrical connector 222 and receptacle 224, the pin and wire count in the ultrasound cable 108 may be reduced to avoid large pin counts and avoid routing so many wires between connectors 212 and 222. In this case, a plurality of ultrasound signals may be serialized or multiplexed onto one signal wire of the ultrasound cable 108.

Figure 7B:
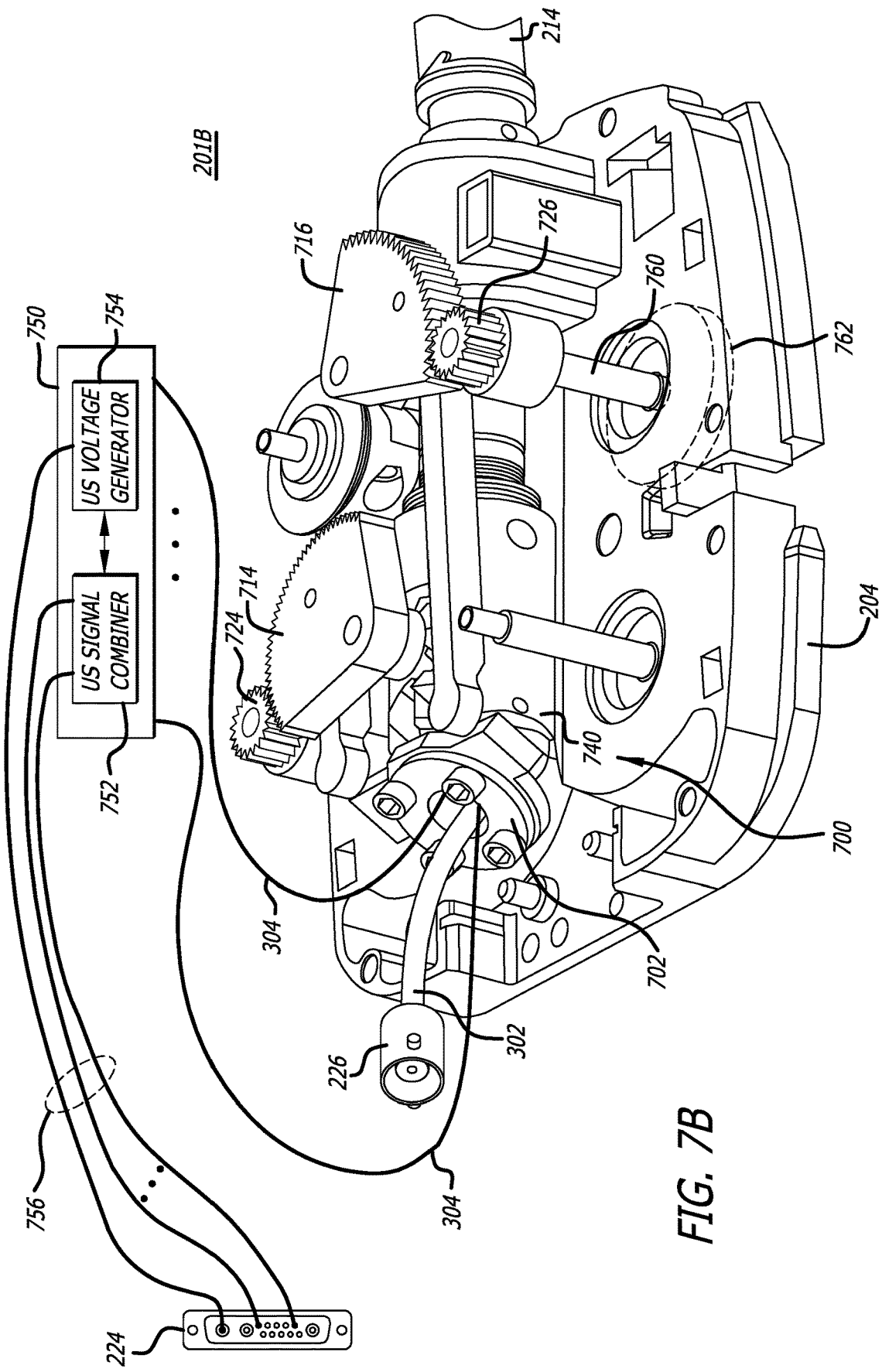

Referring now to FIG. 7B, the mountable housing 201B of the tool 200B is illustrated with its cover 202B removed to show the internal drive mechanisms and cable connections. The mountable housing 201B is similar to the mountable housing 201A but for how the laser cable 106 and the ultrasound cable 108 are coupled there-to.

The mountable housing 201B includes the gimbaled cable actuator 700 previously described herein to manipulate the driver cables 216 to control movement of the wristed joint 218. The description of the gimbaled cable actuator 700 is incorporated here by reference to avoid duplicity.

The mountable housing 201B further includes the ultrasound cable receptacle 224 and the laser cable receptacle 226 mounted to the base 204 and/or the cover 202B. The mountable housing 201B may further include an isolation chamber 203B under the cover 202B to isolate a printed circuit board 750, the electrical connections, and electrical cables from the drive mechanisms or transmission for the drive cables 216.

As previously mentioned, a plurality of ultrasound signals may be serialized or multiplexed onto one signal wire of the ultrasound cable 108. The ultrasound connector 222 couples to the ultrasound receptacle 224 to couple power/signal wires of the ultrasound cable 108 to the power/signal wires 756. The power/signal wires 756 couple to the printed circuit board 750. The printed circuit board 750 includes an ultrasound signal combiner 752 and an ultrasound voltage generator 754 coupled together. The signal wires couple to the ultrasound signal combiner 752. The power wires couple to the ultrasound voltage generator 754.

The signal combiner acts as a multiplexer/demultiplexer and/or serializer/deserializer to combine a plurality of signals from the ultrasound sensors together for communication over fewer parallel wires to the external ultrasound generator/controller. This allows the pin count of the ultrasound connector 222 and the ultrasound receptacle 224 to be less so they are smaller connectors. Additionally, there are fewer wires routed in the ultrasound cable 108.

An end of the ultrasound signal wires 304 are coupled to the printed circuit board 750 and the signal combiner 752 and/or voltage generator 754. The ultrasound signal wires 304, as part of the cable bundle 300, are routed through a center opening in the actuator plate 702, through a hollow center of the parallel linkage 740, and into the shaft 214 of the tool.

The ultrasound transducers 504 are excited by high voltages to generate ultrasound signals. Instead of generating high voltage signals at an external ultrasound generator/controller, it may be more convenient to locally generate the high voltage signals to excite the ultrasound transducers 504. In response to control signals from the signal combiner 752, the ultrasound voltage generator 754 generates a plurality of high voltage signals for exciting the ultrasound transducers 504 to generate the ultrasound signals.

The laser cable receptacle 226 couples to an end of the laser cable 302. The laser cable 302 may be an optical fiber 302A to propagate laser light to the end effector 220A or electrical control wires 302B to power and signal a laser diode 608 in the end effector 220D. In either case, the laser cable 302, as part of the cable bundle 300, is routed through the center opening in the actuator plate 702, through the hollow center of the parallel linkage 740, and into the shaft 214 of the tool for routing to the end effector.

If the laser cable 302 is an optical fiber 302A, the use of the connector 210B and the receptacle 226 may allow it to be readily replaced if damaged or defective to repair the tool. Optical fibers are susceptible to heat damage from excess laser energy as well shock damage from misuse. Optical fibers may also acquire microscopic cracks or breaks if they exceed their maximum radial bend. Once heat damaged or cracked, the optical fiber may not transmit laser energy as efficiently, resulting in decreased laser energy at the working end. If the laser cable 106 is damaged or defective, the use of the connector 210B and the receptacle 226 may allow it to be readily replaced if damaged or defective.

Operation of the Combined Ultrasound-Laser Tool

Figure 8:
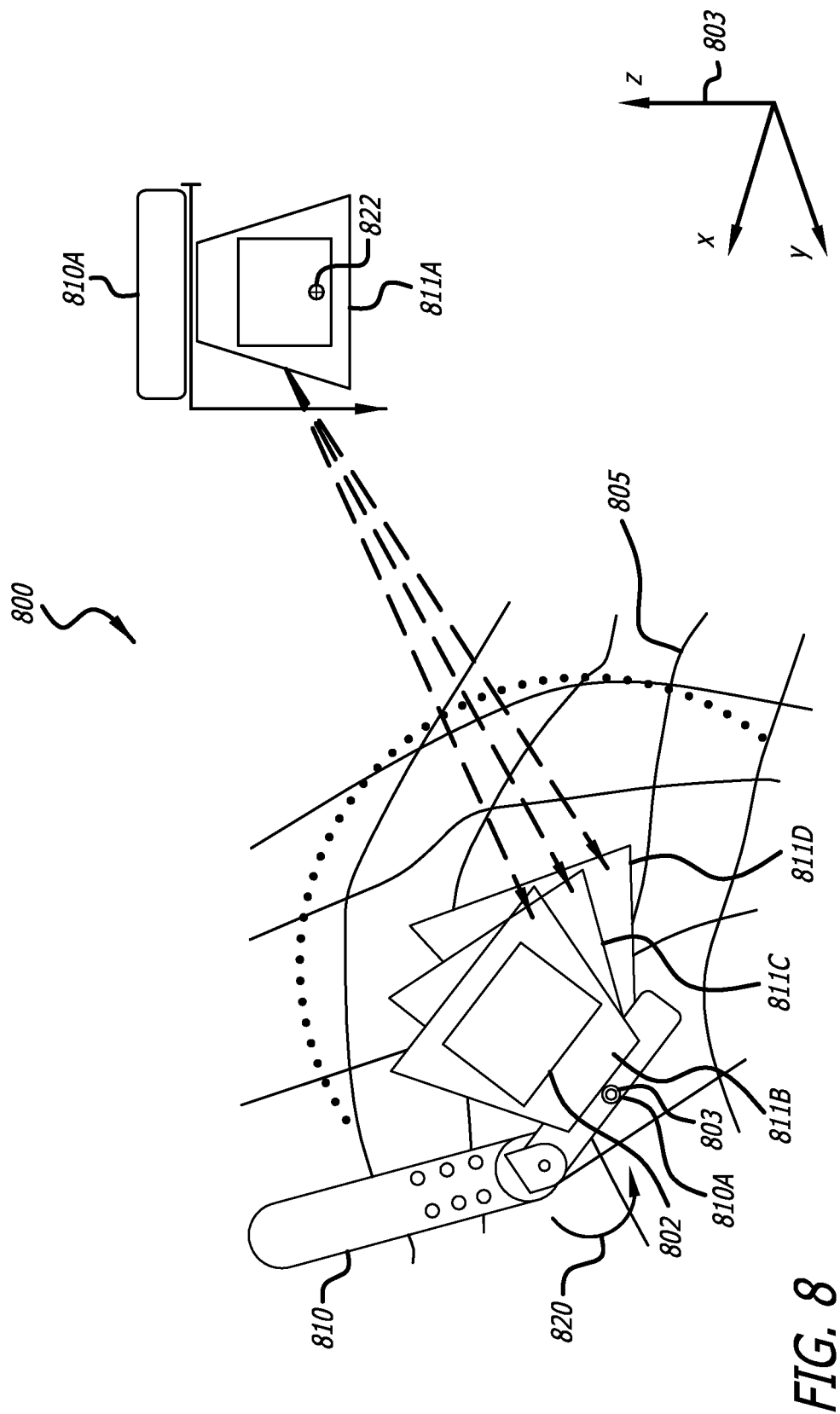
FIG. 8 is a diagram illustrating a combined laser ultrasound robotic surgical tool laser marking tissue in a surgical site.

Referring now to FIG. 8, an illustration depicts an image 800 of the surgical site and the ultrasound picture in picture images that may be displayed in the viewer of the surgeon's console. A two-dimensional or three-dimensional image is displayed on a video screen for the surgeon performing the procedure. Ultrasound images 811B-811D are combined and interpolated by a computer processor into a combined ultrasound image 811A. A targeting dot 822 may be displayed on combined ultrasound image 811A to represent the location where the laser is focused. In one embodiment of the invention, the targeting dot 822 is a computer-generated dot (such as generated by the computer 151A, 151B) that appears only on the display monitor and is not a physical mark in the surgical site.

The targeting dot 822 may be used by the surgeon to aim the marking laser in an ultrasound image. For instance, as mentioned previously, ultrasounds may be used to differentiate healthy cells from cancerous cells. Once masses of cancerous cells are identified on the ultrasound image, a surgeon may begin marking the boundaries of the cancerous cells for later removal. A marking laser may be used to burn a series of dots delineating the boundaries of the cancerous mass. The burn marks would not likely show up on an ultrasound image, so in order to aid the surgeon, a virtual display of the burn marks may be created with some specialized software. Each time the laser is fired a virtual dot may be displayed on the video monitor. In this way, the surgeon may be better able to track their progress as they mark the area to be excised. Once the area is marked, the ultrasound images may be removed from the video monitor displaying video images of the surgical site. The burn marks should be optically visible by the camera and shown in the video display to provide the surgeon with an accurate map of the area to be excised.

In another embodiment of the invention, a cutting laser such as a CO2 laser may be deployed at the ultrasound probe. Once again, the targeting dot 822 may be used by the surgeon to guide the laser cutter. A virtual image of the cut line may be created by software and superimposed on ultrasound image 811A to aid the surgeon in guiding the laser.

Figure 9:
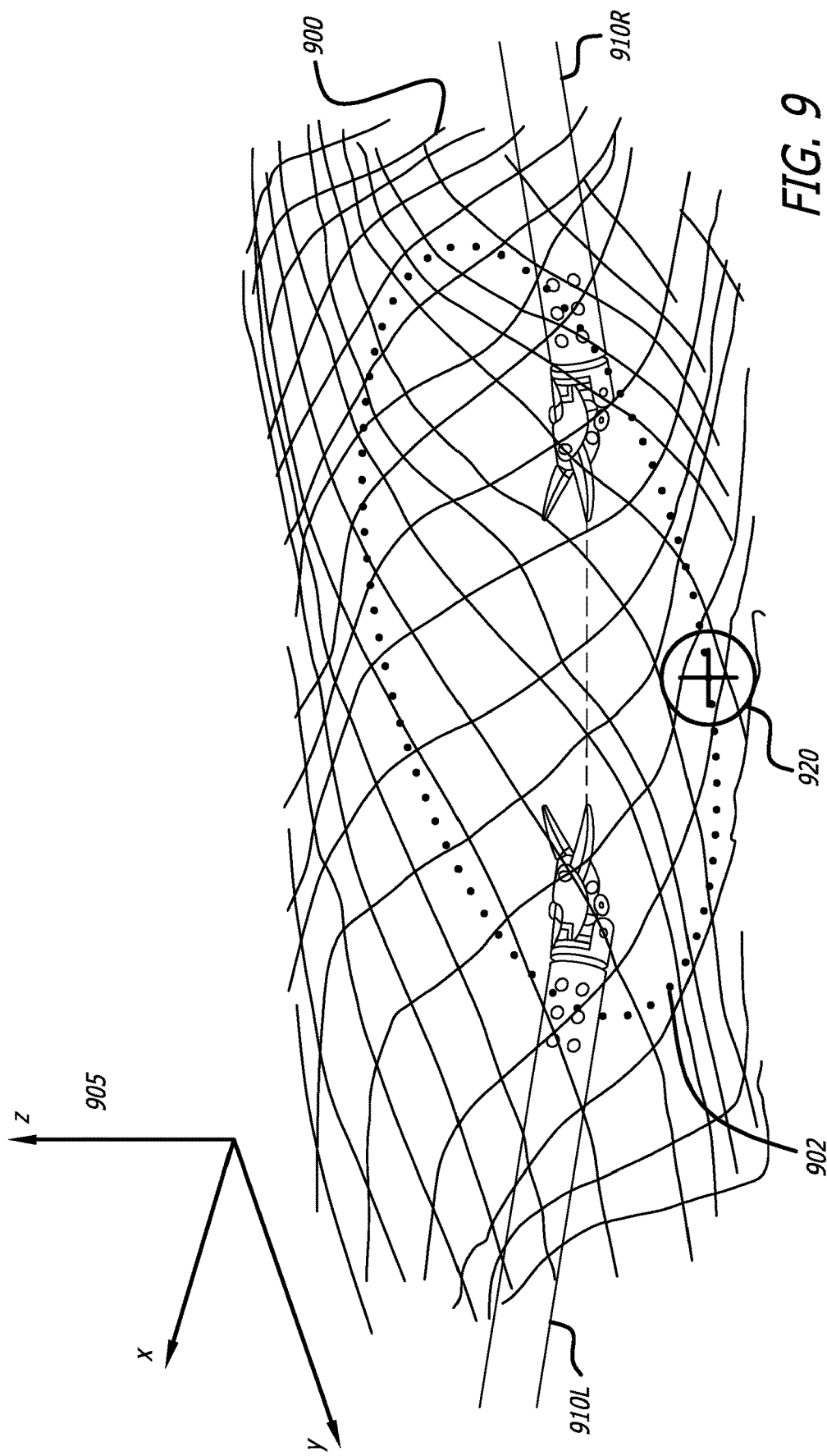
FIG. 9 is a diagram illustrating the laser marking on tissue in the surgical site indicating where a surgeon may perform a minimally invasive surgical procedure with one or more robotic surgical tools.

Referring now to FIG. 9, an image of the surgical site 900 is illustrated after laser marking has been completed. The dotted line 902 represents burn marks made on tissue by a laser that was guided by ultrasound imagery. The laser marked tissue can reduce the time spent looking for tissue that requires surgery. Robotic surgical tools 910L and 910R, such as robotic surgical scissors, may be readily moved into the marked area to perform surgery therein.

The added functionality provided by a combined laser/imaging tool may improve the efficiency of a surgeon and thereby lower the costs of minimally invasive surgical procedures. With a four arm robotic surgical system or the like, an endoscopic camera tool and an ultrasound imaging tool with lasers are available while a surgeon performs surgery with his left and right hands controlling tissue manipulative robotic surgical tools (e.g., monopolar scissor, and a bipolar grasper). With the laser/ultrasound combination, a surgeon may have three types of energy (monopolar, bipolar, and laser) to apply to tissue, two imaging capabilities (camera and ultrasound, with picture in picture) and two mechanical tools (cutting and grasping) for combined seven tools using only four robotic surgical arms.

Robotically Controlled Endoscopic Camera with Laser Cutting Tool

To perform minimally invasive surgery in areas around the neck and throat, a robotic surgical system that can use the openings provided by the nose or throat may be preferable. However, this limits the number of openings through which robotic surgical tools may be inserted. The robotic surgical tools are made smaller so that a plurality of robotic surgical tools may pass through a single opening. To gain even more surgical capability through the one opening, the robotic surgical tools may be multitasking in their capabilities.

Previously described herein was a combined ultrasound-laser robotic surgical tool. A combined laser-endoscopic camera robotic surgical tool is now described to provide multiple surgical capabilities in one robotic surgical tool.

Figure 10:
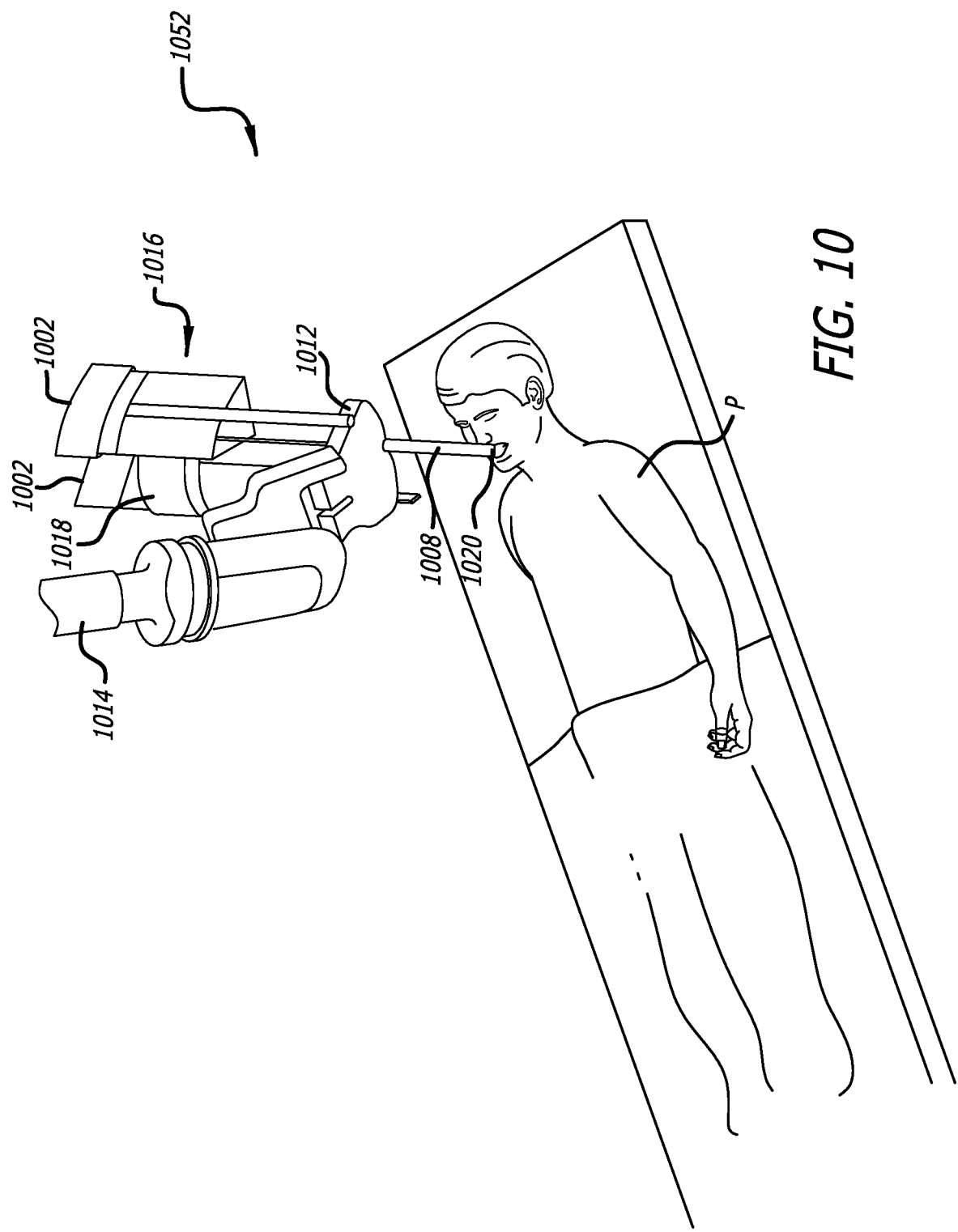
FIG. 10 is a perspective view of a portion of a robotic patient-side system with a combined laser imaging robotic surgical tool for minimally invasive surgery through a single port.

Referring now to FIG. 10, a portion of a patient side cart 1052 is illustrated with an actuating end 1016 of a robotic or manipulating arm 1014. But for a single robotic arm 1014, other portions of the patient side cart 1052 may be similar to the patient side cart 252 illustrated in FIG. 1B to support the actuating end 1016 over a patient P. The robotic arm 1014 may be coupled to a set-up arm. The robotic surgical system including the patient side cart 1052 may be similar to the robotic surgical systems illustrated in FIGS. 1A and 1C including the one or more control consoles and the laser/generator controller.

The general function of the actuating end 1016 of the robotic or manipulating arm 1014 and the robotic surgical tools coupled thereto are described in more detail in U.S. patent application Ser. No. 11/762,165 entitled MINIMALLY INVASIVE SURGICAL SYSTEM filed by Larkin et al. on Jun. 12, 2007 which is incorporated herein by reference.

A single guide tube 1008 of the actuating end 1016 of the robotic arm is used to insert the tools 1002A, 1002B, and 1018 into an opening into the patient P, such as the patient's mouth for example. The guide tube 1008 is coupled to the platform 1012 which is in turn moveably coupled to the robotic arm 1014 by one or more actuator mechanisms for pitch, yaw, roll, and insertion along an insertion axis of the guide tube. The guide tube 1008 may be maintained in a fixed position or rotated (e.g., pitch, yaw, and/or roll) around a remote center point 1020 near the opening into the patient if permitted by the circumstances, including the tissue in the body where the tools may be located.

The robotic surgical tool 1018 that is more fully inserted into the guide tube 1008 is a combined laser ablation-imaging robotic surgical tool to provide multiple capabilities in one instrument. The two other robotic surgical tools 1002A-1002B are illustrated as being partially inserted into the guide tube 1008 in FIG. 10. The robotic surgical tools 1002A-1002B may be different types of robotic surgical tools than the combined laser ablation-imaging robotic surgical tool 1018. The combined laser ablation-imaging robotic surgical tool 1018 efficiently uses the available opening provided by the singular guide tube 1008.

Figure 11:
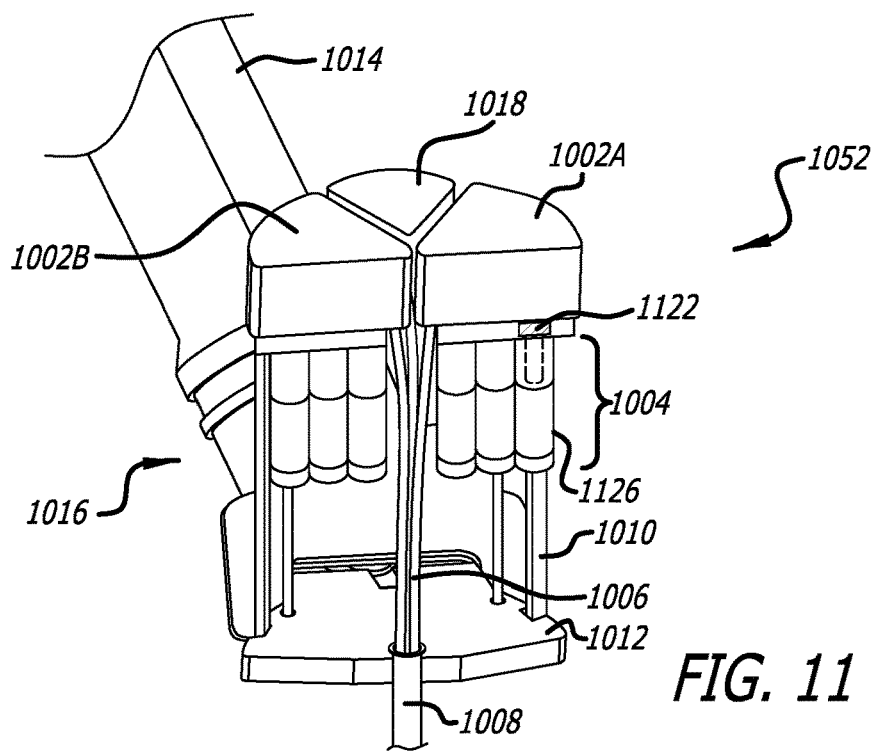
FIG. 11 is another perspective view of the portion of the robotic patient-side system of FIG. 10 with the combined laser imaging robotic surgical tool.

Referring now to FIG. 11, a proximal end of the robotic surgical tools 1018, 1002A-1002B are shown inserted into the guide tube 1008 and coupled to a tool actuator assembly 1004. Each tool 1018, 1002A, 1002B may include a body tube 1006 inserted into the guide tube 1008. The tool actuator assembly 1004 is mounted to a linear actuator 1010 (e.g., a servo-controlled lead screw and nut, or a ball screw and nut assembly) that independently controls each tool's further insertion within guide tube 1008 along with its body tube's 1006. The guide tube 1008 may be removeably mounted to the support platform 1012. Removable and replaceable guide tubes allow different guide tubes designed for use with different procedures to be used with the same telemanipulative system (e.g., guide tubes with different cross-sectional shapes or various numbers and shapes of working and auxiliary channels).

The actuator assembly 1004 mates with and actuates components in the robotic surgical tools 1018, 1002A-1002B. The actuator assembly 1004 includes a plurality of rotatable servomotor actuators 1126 coupled to actuator disks 1122. Each actuator disk 1122 includes holes to interface to pins of rotatable interface disks of the robotic surgical tools. Each actuator disk 1122 is rotated in response to servo control inputs to control the robotic surgical tool.

Figure 12:
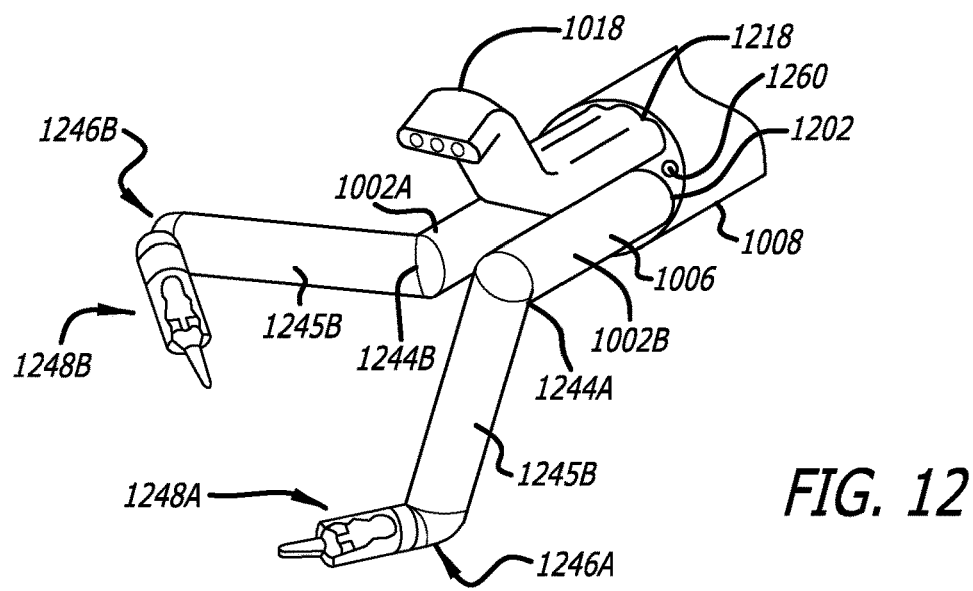
FIG. 12 is a perspective view of a distal end portion of the robotic patient-side system of FIG. 10 with the combined laser imaging robotic surgical tool.

Referring now to FIG. 12, a distal end of the robotic surgical tools 1018, 1002A-1002B is shown extending out from the guide tube 1008. The guide tube 1008 includes a channel 1218 and a pair of channels 1202 through which the respective robotic surgical tools 1018 and 1002A-1002B may be inserted and extend. The guide tube 1008 may further include an auxiliary channel 1260 through which other robotic surgical tools may be introduced or withdrawn, such as irrigation, suction, or cleaning devices for example. As illustrated in FIG. 12, the body tube 1006 of each respective robotic surgical tool 1018, 1002A-1002B may extend out from the respective channels of the guide tube 1008. With for the guide tube 1008 entering natural orifices of a body, its diameter and the diameter of each respective robotic surgical tool 1018, 1002A-1002B is limited. By providing more than one capability to a robotic surgical tool, the limited diameter of the guide tube is more efficiently utilized. Moreover, a tool change may be reduced or eliminated by combining more than one capability into a robotic surgical tool.

Each of the respective robotic surgical tools 1002A-1002B include end effectors 1248A-1248B coupled to the body tube 1006 by one or more joints 1244A-1244B, 1246A-1246B, and a parallel tube 1245A-1245B. In one instance, the body tube 1006 for the robotic surgical tools 1002A-1002B is approximately 7 mm in diameter. In another instance, the body tube 1006 for the robotic surgical tools 1002A-1002B is approximately 5 mm in diameter.

The combined laser ablation-imaging robotic surgical tool 1018 is now described in more detail.

Figure 13:
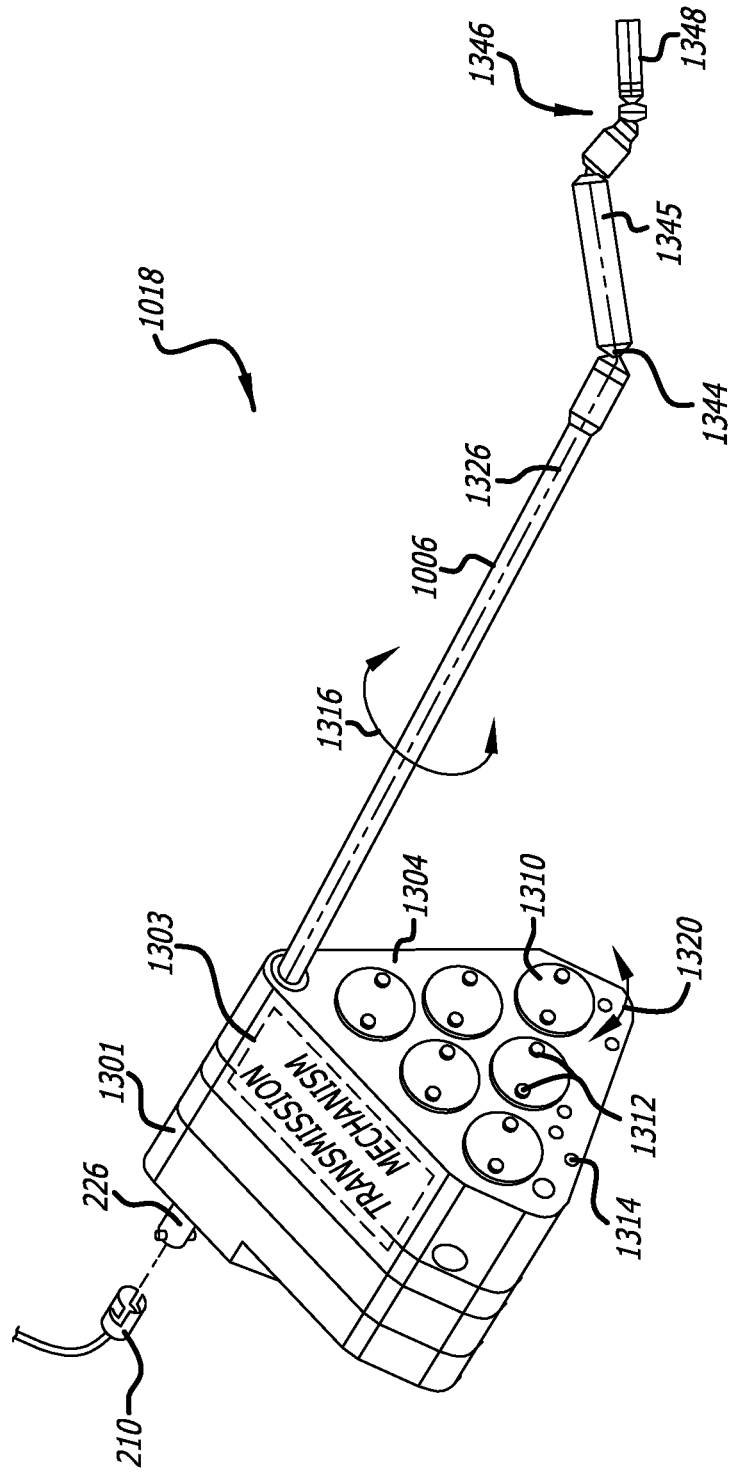
FIG. 13 is a perspective view of the combined laser imaging robotic surgical tool for use with the robotic patient side system of FIG. 11.
Figure 14A:
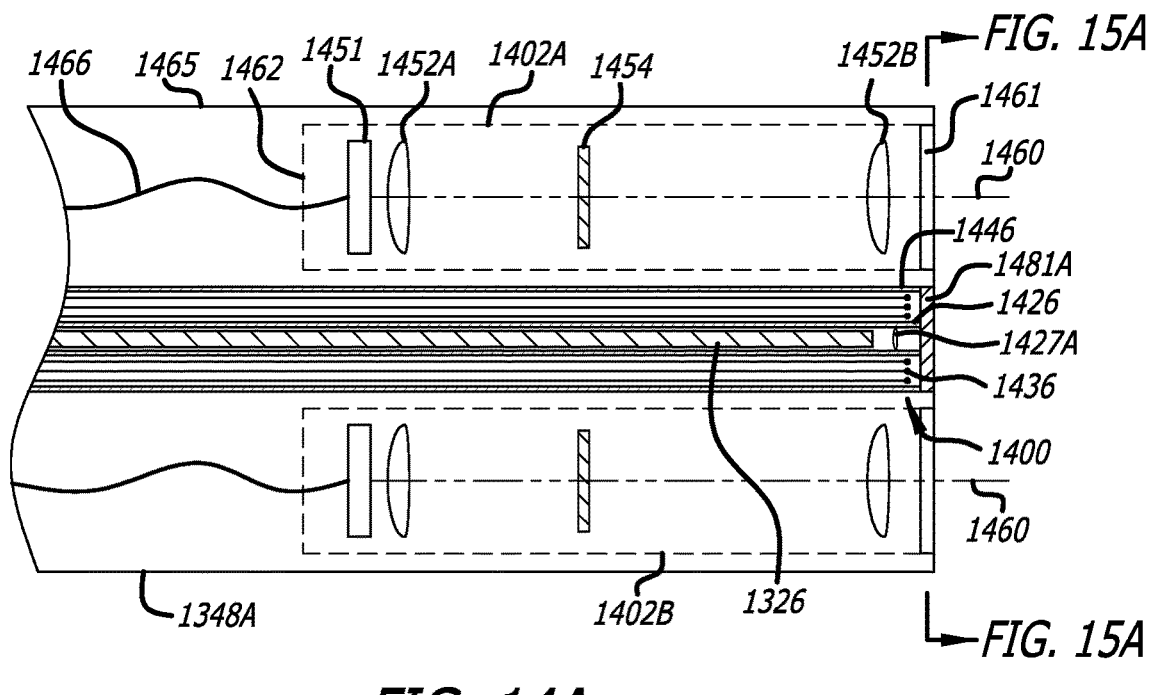
FIGS. 14A-14B are cutaway side views of embodiments of the end effector of the combined laser imaging robotic surgical tool.

Referring now to FIG. 13, a perspective view of the combined laser ablation-imaging robotic surgical tool 1018 is illustrated. The combined laser ablation-imaging robotic surgical tool 1018 includes a housing 1301 with a mountable base 1304, a transmission mechanism 1303, a shaft or body tube 1006, and an end effector 1348 coupled together. The housing 1301 and the transmission mechanism 1303 are coupled to the proximal end of the body tube 1006 while the end effector 1348 is coupled to the distal end of the body tube 1006. The end effectors 1348 may couple to the body tube 1006 by one or more joints 1344, 1346, and a parallel tube 1345. The one or more joints may be wristed joints, such as the segmented wristed joint described previously with reference to FIG. 4. The shaft or body tube 1006 for the combined laser ablation-imaging robotic surgical tool 1018 may or may not be cylindrically shaped.

The transmission mechanism 1303 provides a mechanical interface for the tool and includes a plurality of rotatable interface disks 1310. One or more the rotatable interface disks 1310 are associated with a degree of freedom of the combined laser ablation-imaging robotic surgical tool 1018. For example, a rotatable interface disk 1310 may be associated with instrument body roll degree of freedom illustrated by the doubled-headed arrow 1316. The rotatable interface disks 1310 may be arranged for compactness, such as the triangular shape as shown for example. Each rotatable interface disk 1310 includes a pair of spaced apart raised pins 1312. The raised pins 1312 of each rotatable interface disk may be spaced eccentrically to provide proper disk orientation when mated with an associated actuator disk.

The transmission mechanism 1303 includes a plurality of mechanical components (e.g., gears, levers, gimbals, cables, etc.) to convert roll torques 1320 received by the rotatable interface disks 1310 and transmit the torque into movement of the components of the combined laser ablation-imaging robotic surgical tool 1018, such as roll 1316 in the body tube 1006 or pitch in the end effector 1348, for example. One or more cables, cable loops, hypotubes, and/or any combination thereof within the body tube may be used to transfer the torque received by the transmission mechanism 1303 to the components at the distal end of the tool, such as the pitch movement of the end effector 1348.

The housing 1301 includes one or more electronic interface connectors 1314 to provide an electronic interface for the combined laser ablation-imaging robotic surgical tool 1018. One or more of the electronic interface connectors 1314 are used to interface to one or more cameras in the end effector 1348.

One or more of the electronic interface connectors 1314 may be used to pass information stored in a semiconductor memory integrated circuit to the master control console regarding the tool and its end effectors. Such passed information may include instrument type identification, number of instrument uses, and the like. The control system may used to update the stored information (e.g., to record number of uses to determine routine maintenance scheduling or to prevent using an instrument after a prescribed number of times).

One or more of the electronic interface connectors 1314 may be used to connect to a power supply or a laser generator to provide power for electronics in the tool, such as a laser diode. Alternately, a power connection may be positioned elsewhere in the housing 1301 on the tool 1018. Other connectors for, e.g., optical fiber lasers, optical fiber distal bend or force sensors, irrigation, suction, etc. may be part of the housing 1301.

One or more of the electronic interface connectors 1314 may also be used to interface to a laser diode in the end effector 1348 in one embodiment of the invention. The electronic interface connector 1314 can couple electrical cables together so that the laser diode can couple to a laser controller 102B to control the laser diode.

In another embodiment of the invention, the housing may include a receptacle 226, such as a BNC receptacle 226, coupled to a fiber optic cable leading to an end of the end effector 1348. A BNC connector 210 connects to the BNC receptacle 226 to couple fiber optic cables together to route laser energy from a laser generator 102B into a fiber optic cable 1326 within the tool. The fiber optic cable 1326 routes the received laser energy through the tool to the end of the end effector 1348. Depending upon the life expectancy of the overall tool and fiber optic cable 1326 used for lasing, the cable 1326 may be readily replaceable. If the expected life expectancy of the fiber optic cable 1326 exceeds that of the overall tool, the cable 1326 may not need to be easily replaceable and be more integrated into the tool to lower costs. On the other hand, if the expected life expectancy of the fiber optic cable 1326 were only one surgery, it would be designed to be readily replaceable. Other fiber optic cables (see FIGS. 14A-15A) may be used to transmit lower light energy to provide lighting within a body cavity for the one or more cameras in the tool 1018 to capture video images.

End Effector for Image Capture and Laser Cutting

FIGS. 14A-14B and 15A-15B respectively illustrate alternate embodiments of the end effector 1348 (end effectors 1348A, 1348B) of the combined laser ablation-imaging robotic surgical tool 1018.

Referring now to FIG. 14A-15A, the combined laser ablation-imaging robotic surgical tool 1018 includes a fiber optic bundle 1400 terminating at the end effector 1348A, and one or more cameras 1402A-1402B. The fiber optic bundler 1400 includes the fiber optic cable 1326 within a channel 1426, and a plurality of light pipes or fiber optic cables 1436 bundled together around the channel 1426 by a sheath 1446. Alternatively, the plurality of light pipes or fiber optic cables 1436 may be bundled together and routed through separate channels within the tool 1018. Light for the plurality of light pipes or fiber optic cables 1436 may be generated by one or more light emitting diodes (LED) in the tool such as to the diode 708 illustrated in FIG. 7A, or alternatively generated by an external illuminator such as a Xenon short-arc lamp, or by other well-known means. Alternatively, one or more light emitting diodes (LED) may be included as part of the end effector, space permitting, instead of the using the plurality of light pipes or fiber optic cables 1436.

The fiber optic cable 1326 can carry sufficient laser energy from the laser generator 102B to laser cut or ablate tissue. The laser energy from the laser generator 102B, transmitted in the fiber optic cable 1326 and coupled to tissue, may be less in order to mark the tissue in the body. That is, the laser energy may be selected for laser marking of tissue. A focusing lens or lens system 1427A may be located between the distal end of the fiber optic cable 1326 and the inside surface of the transparent cover or window 1481A, and functions to collimate the laser light diverging from the fiber optic cable 1326, or to focus it in order to attain maximum energy density at a desired distance from the external surface of the transparent cover or window 1481A. The channel 1426 may facilitate the replacement of the fiber optic cable 1326 if the need arises. The number of light pipes or fiber optic cables 1436 in the tool 1018 is such that if a couple fail, the lighting supplied by those still functioning is sufficient for the one or more cameras to continue capturing images. The cameras sensitivity may also be able to compensate for some loss of lighting due to the failed light pipes or fiber optic cables 1436.

The one or more cameras 1402A-1402B each include an image sensor 1451 (e.g., charge coupled device array), one or more lenses 1452A-1452B, and a transparent cover 1461 aligned together along an optical axis 1460 by a housing 1462. The image sensor 1451 captures images from light passing through the transparent cover. The one or more lenses 1452A-1452B capture light from the objects in the surgical field, and focus it into the image sensor 1451. The transparent cover 1461 may be hermetically sealed to the camera housing 1462 and/or the end effector enclosure 1465.

Each of the one or more cameras 1402A-1402B may further include a filter 1454 aligned to the optical axis 1460 by the housing 1462 before the light rays reach the image sensor 1451. The filter 1454 may be used to filter out excessive light generated by the laser generator for laser cutting. The filter 1454 may be particularly tuned to filter out the wavelength of light used for laser cutting while allowing lights of other wavelengths to pass through into the image sensor 1451. For example, the laser may be chosen to emit a 532 nm wavelength (green laser light) over a power range of about 25-60 watts. To avoid the laser light from saturating the image sensor 1451 in each video camera 1402A-1402B, the filter 1454 may be tuned to filter out green light around a wavelength of 532 nanometers.

An electrical cable 1466 may be coupled to the image sensor 1451 of each of the one or more cameras 1402A-1402B to provide power to the image sensor 1451 and transfer digital data of the captured images through the tool 1018 to the control consoles 150A-150B. One of the one or more electronic interface connectors 1314 may couple to the electrical cables 1466 to facilitate the removal and replacement of the combined laser ablation-imaging robotic surgical tool 1018.

Figure 15A:
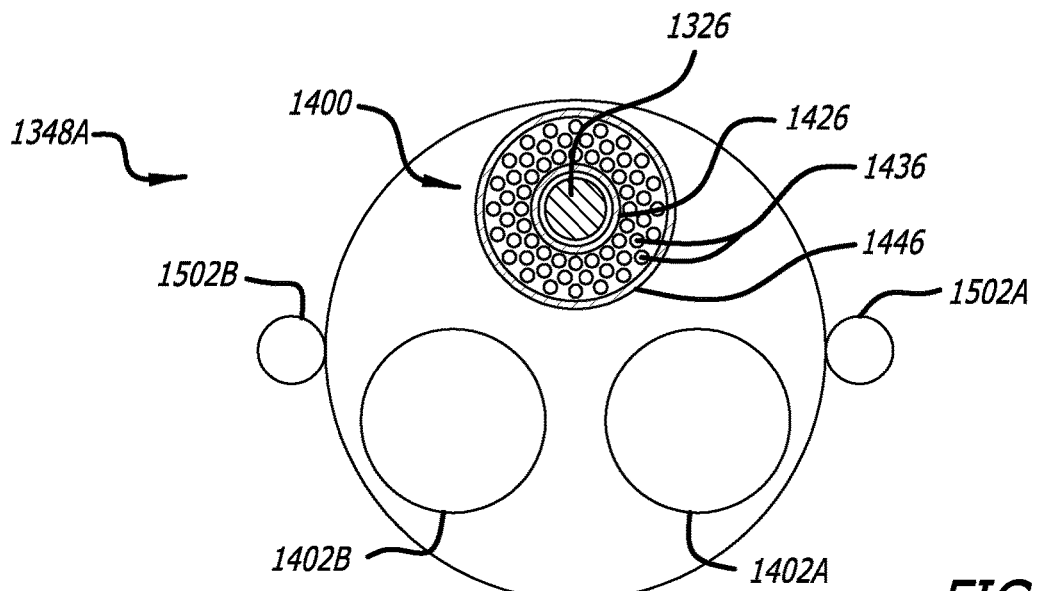
FIGS. 15A-15B are bottom views of the embodiments of the end effector of FIGS. 14A-14B, respectively.

Referring now to FIG. 15A, the end effector 1348A may include one or more alignment tabs 1502A-1502B as part of the enclosure 1465. The one or more alignment tabs may extend along the body of the tool 1018 so that the one or more cameras and each image sensor 1451 is retained in alignment with the end effector 1348 and its controlled movement.

Figure 14B:
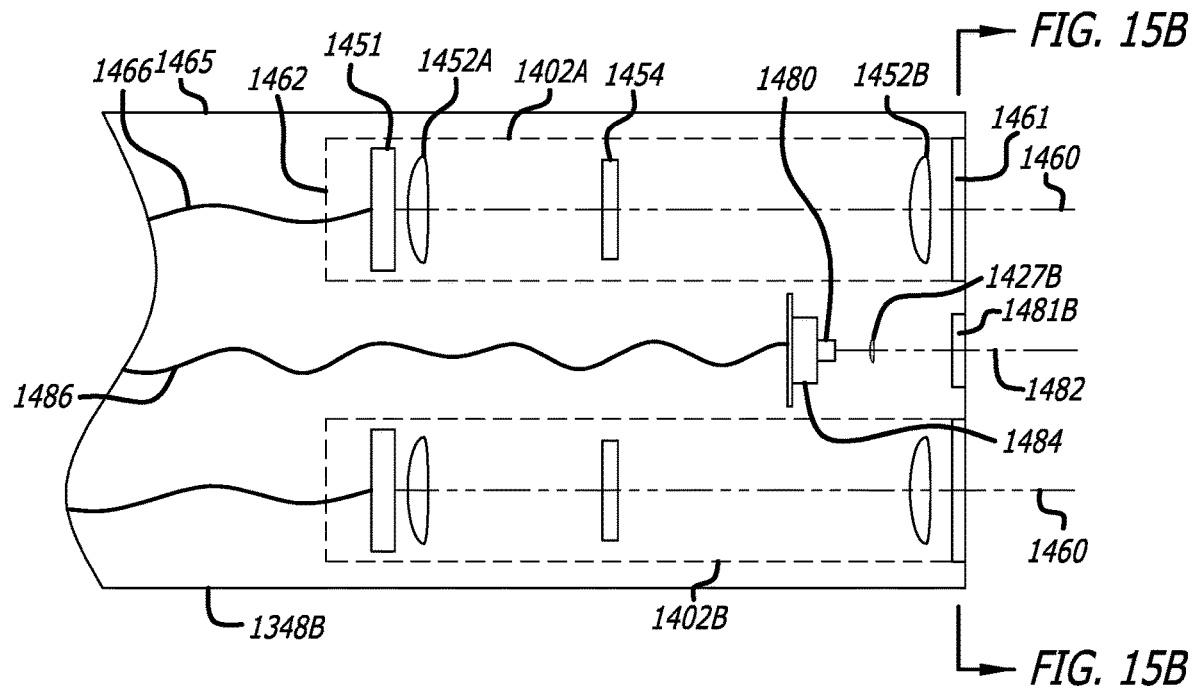
Figure 15B:
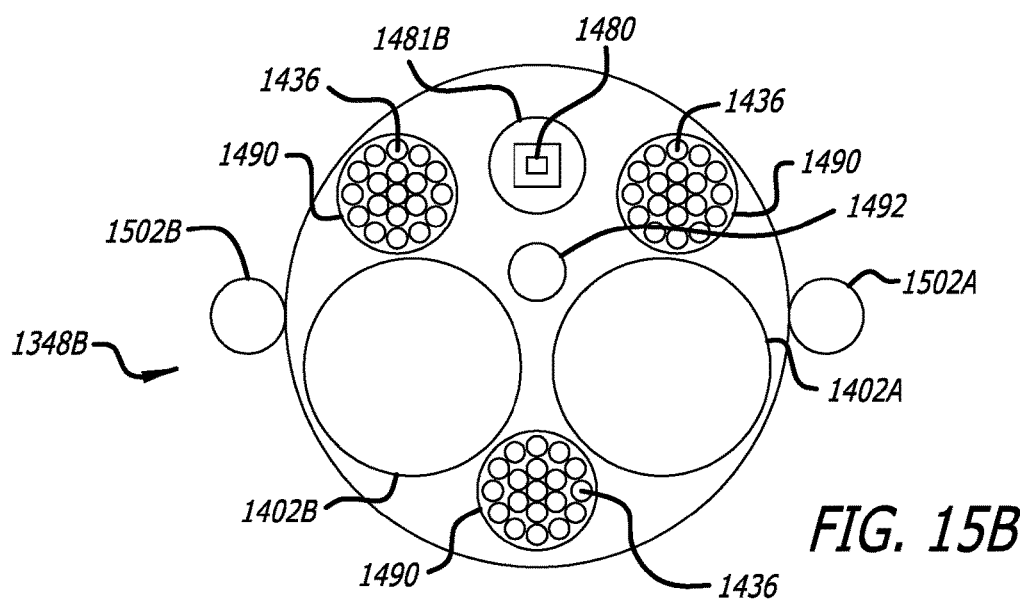

Referring now to FIG. 14B-15B and the end effector 1348B, the combined laser ablation-imaging robotic surgical tool 1018 at its distal end includes the one or more cameras 1402A-1402B and a laser diode 1480 instead of the fiber optic cable. The plurality of light pipes or fiber optic cables 1436 are bundled together into one or more channels 1490 as illustrated in FIG. 15B to provide lighting for the one or more cameras 1402A-1402B. A transparent cover may be hermetically sealed to the enclosure 1465 over the end of the plurality of light pipes or fiber optic cables 1436 to avoid body fluids from seeping into the end effector so that the tool can be readily sterilized. Light for the plurality of light pipes or fiber optic cables 1436 may be generated by one or more light emitting diodes (LED) in the tool such as to the diode 708 illustrated in FIG. 7A, or alternatively generated by an external illuminator such as a Xenon short-arc lamp, or by other well-known means. Alternatively, one or more light emitting diodes (LED) may be included as part of the end effector, space permitting, instead of the using the plurality of light pipes or fiber optic cables 1436.

As shown in FIG. 14B, the laser diode 1480 is coupled to one end of an electrical cable 1486 to provide power and to control the generation of the laser light along an optical axis 1482. Another end of the electrical cable 1486 is coupled to one or more of the electronic interface connectors 1314 of the tool 1018 to couple to a laser controller, such as the laser controller/generator 102B illustrated in FIGS. 1A, 1C.

From the laser diode 1480, laser light passes through a transparent cover or window 1481B and out of the tool into a body cavity. The transparent cover 1481B may be hermetically sealed to the enclosure 1465 of the end effector 1348B to avoid body fluids from seeping into the end effector so that the tool can be readily sterilized. A focusing lens or lens system 1427B may be located between the active region of the laser diode 1480 and the inside surface of the transparent cover or window 1481B, and functions to collimate and or focus the laser light diverging from the active region of the laser diode, or to focus it in order to attain maximum energy density at a desired distance from the external surface of the transparent cover or window 1481B.

When lasing, the laser diode 1480 may generate heat. The laser diode 1480 may be coupled to a heat removal device 1484, such as a passive heat sink or slug. Additionally or alternatively, a fluid channel 1492 may be routed through the tool 1018 adjacent the laser diode 1480 to transfer heat away from it. The fluid may also flow through the channel and out of the tool 1018 into a body cavity to irrigate it. If the channel is under suction, fluid may flow out of the body cavity into the channel 1492, along the laser diode 1480 to cool it, and out of the tool 1018. If the laser diode 1480 is of sufficiently low power, liquid cooling by a fluid channel may be unnecessary.

A similar fluid channel may be made available in the combined laser-ultrasound tool to cool down a heated ultrasound probe. However, as the ultrasound tool may be in front of the combined laser-camera tool, the fluid channel 1492 of the combined laser-camera tool or a dedicated suction/irrigation tool may be used to douse the ultrasound probe with a cool liquid to remove heat there-from.

Referring now to FIG. 9, the combined laser-endoscopic camera tool 1018 captures images of a surgical site for display in the viewer of the surgeon's console. A bulls eye 920 may be computer generated and overlaid onto the images of the surgical site for display in the viewer. The bulls eye 920 may indicate the point where the laser can mark or cut tissue within the field of view of the surgical site. As an endoscopic camera is usually used to capture images of a surgical site, combing the laser with the camera provides an additional tool that a surgeon may use to cut tissue without using additional cannulas or ports of entry into the surgical site.

Moreover, with reference to FIGS. 1D and 9, one surgeon O operating at a first console 150A may be manipulating the tools 910L, 910R within the surgical site 900 while another surgeon M may be operating the laser of the combined laser-endoscopic camera tool 1018 at a second console 150B. The second surgeon operating the combined laser-endoscopic camera tool may help reduce the time spent performing a minimally invasive surgery.

CONCLUSION

While this specification includes many specifics, these should not be construed as limitations on the scope of the disclosure or of what may be claimed, but rather as descriptions of features specific to particular implementations of the disclosure. Certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. The claimed invention is limited only by patented claims that follow below.

What is claimed is:

1. A robotic surgical system comprising:
a patient side cart having a plurality of robotic arms;
a combined laser ablation-imaging surgical tool mounted to a first robotic arm of the patient side cart, the combined laser ablation-imaging surgical tool having a wristed joint and an end effector coupled to the wristed joint, the end effector having a laser emitting device to direct a laser beam onto tissue in a surgical site and an image capturing device to capture video images of the tissue in the surgical site, the laser emitting device and the image capturing device mounted in a hermetically sealed enclosure with an aperture;
a first control console in communication with the combined laser ablation-imaging surgical tool to receive the captured video images of tissue in the surgical site, the first control console to display the captured video images on a first display device to a first user and one or more processors within the first control console configured to generate a computer generated targeting dot overlaid on the captured video images, the computer generated targeting dot representing a location where the laser beam from the laser emitting device is focused; and
a laser generator/controller coupled to the combined laser ablation-imaging surgical tool and the first control console, the laser controller/generator to control the emission of the laser beam onto tissue of the surgical site by the combined laser ablation-imaging surgical tool in response to a control signal.

2. The robotic surgical system of claim 1, further comprising:
an ultrasound camera coupled to a second robotic arm of the patient side cart, the ultrasound camera in communication with the first control console, the ultrasound camera to capture ultrasound images of the surgical site and communicate the captured ultrasound images to the first control console; and
wherein the video images are displayed on the first display device and the ultrasound images are displayed picture-in-picture on the first display device.

3. The robotic surgical system of claim 2, further comprising:
an ultrasound generator/controller in communication with the first control console and the ultrasound camera, the ultrasound generator/controller to generate ultrasound signals to excite the ultrasound probe to emit ultrasound waves onto the tissue in the surgical cite, the ultrasound probe to capture return ultrasound waves to generate received signals, the ultrasound generator/controller to translate the received signals into the ultrasound images for display on the first display device.

4. The robotic surgical system of claim 1, wherein
the image-capturing device is a stereo video camera and the captured images are stereo video images of the surgical site.

5. The robotic surgical system of claim 1, further comprising
a second display device coupled in communication with the patient side cart and the combined laser ablation-imaging surgical tool, the second display device to receive the captured video images of tissue in the surgical site and display them to a second user.

6. The robotic surgical system of claim 1, further comprising:
a second control console having a second display device, the second control console in communication with the combined laser ablation-imaging surgical tool to receive the captured images of tissue in the surgical site and display the captured images on the second display device to a second user;
wherein the first user to generate control signals to control the laser generator/controller and the combined laser ablation-imaging surgical tool to position and emit the laser light to mark tissue such that it is visible to a video camera;
wherein the second control console is in communication with a second surgical tool coupled to a second robotic surgical arm and a third surgical tool coupled to a third robotic surgical arm of the patient side cart, and
wherein the second user to perform surgery on the tissue in the surgical site in response to the marked tissue.

7. A robotic surgical system comprising:
a combined laser ablation-imaging surgical tool including
a mountable housing having a base and at least a first actuator and a second actuator mounted to the base, the base adapted to mount to a robotic surgical arm to actuate the first actuator and the second actuator,
a hollow shaft having a first end rotatably coupled to the mountable base, the hollow shaft to extend into a surgical site and rotate in response to the first actuator,
a wristed joint having a first end coupled to a second end of the hollow shaft, a second end of the wristed joint to move in response to the second actuator, and
an end effector coupled to the second end of the wristed joint to concurrently move with the second end of the wristed joint, the end effector including
a hermetically sealed enclosure having an aperture with a transparent cover hermetically sealing over the aperture,
a laser-emitting device mounted in the enclosure near the aperture, the laser-emitting device configured to emit laser light out to a surgical site through the aperture,
an image capturing device to capture video images of tissue in the surgical site, and
a plurality of light pipes to illuminate the surgical site;
a first control console in communication with the combined laser ablation-imaging surgical tool to receive the captured video images of tissue in the surgical site, the first control console to display the captured video images on a first display device to a first user and one or more processors within the first control console configured to generate a computer generated targeting dot overlaid on the captured video images, the computer generated targeting dot representing a location where the laser beam from the laser emitting device is focused; and
a laser generator-controller coupled in communication with the combined laser ablation- imaging surgical tool and the first control console, the laser generator-controller to control the emission of the laser beam onto tissue of the surgical site by the combined laser ablation-imaging surgical tool in response to a control signal.

8. The robotic surgical system of claim 7, wherein
the image-capturing device is a stereo video camera and the captured images are stereo video images of the surgical site.

9. The robotic surgical system of claim 7, wherein
the image-capturing device further comprises a filter aligned to the optical axis before an image sensor to filter out excessive light generated by the laser generator-controller.

10. The robotic surgical system of claim 9, wherein
the filter is tuned to filter out the wavelength of light used by the laser emitting device while allowing lights of other wavelengths to pass through into the image sensor.

11. The robotic surgical system of claim 7, wherein
the end effector further comprises a heat removal device.

12. The robotic surgical system of claim 11, wherein
the heat removal device is a fluid channel routed through the surgical tool.

13. The robotic surgical system of claim 7, further comprising:
an ultrasound camera coupled to a second robotic arm and the first control console, the ultrasound camera to capture ultrasound images of the surgical site and communicate the captured ultrasound images to the first control console; and
wherein the video images are displayed on the first display device and the ultrasound images are displayed picture-in-picture on the first display device.

14. The robotic surgical system of claim 13, further comprising:

an ultrasound generator/controller coupled to the first control console and the ultrasound camera, the ultrasound generator/controller to generate ultrasound signals to excite the ultrasound probe to emit ultrasound waves onto the tissue in the surgical cite, the ultrasound probe to capture return ultrasound waves to generate received signals, the ultrasound generator/controller to translate the received signals into the ultrasound images for display on the first display device.

15. The robotic surgical system of claim 7, further comprising a patient side cart coupled in communication with the first control console, the patient side cart including a plurality of arms with the combined laser ablation-imaging surgical tool mounted to a first arm of the plurality of arms.

16. The robotic surgical system of claim 15, further comprising:

a second control console in communication with the combined laser ablation-imaging surgical tool to receive the captured images of tissue in the surgical site and display the captured images on a second display device to a second user;

wherein the first user to generate control signals to control the laser generator/controller and the combined laser ablation-imaging surgical tool to position and emit the laser light to mark tissue such that it is visible to a video camera; and wherein the second control console is in communication with a second surgical tool coupled to a second robotic surgical arm and a third surgical tool coupled to a third robotic surgical arm of the patient side cart, and the second user to perform surgery on the tissue in the surgical site in response to the marked tissue.

17. The robotic surgical system of claim 15, further comprising:

a second display device coupled in communication with patient side cart and the combined laser ablation-imaging surgical tool, the second display device to receive the captured video images of tissue in the surgical site and display them to a second user.

* * * * *